(12) United States Patent
Kobylevsky et al.

(10) Patent No.: US 7,848,934 B2
(45) Date of Patent: Dec. 7, 2010

(54) REMOTE PRESCRIPTION REFILL SYSTEM

(75) Inventors: Paul Kobylevsky, Flushing, NY (US); Valery Gurovich, Ramsey, NJ (US)

(73) Assignee: Telemanager Technologies, Inc., Newark, NJ (US)

( * ) Notice: Subject to any disclaimer, the term of this patent is extended or adjusted under 35 U.S.C. 154(b) by 1123 days.

(21) Appl. No.: 09/858,877

(22) Filed: May 15, 2001

(65) Prior Publication Data
US 2002/0052762 A1 May 2, 2002

Related U.S. Application Data

(63) Continuation-in-part of application No. 09/097,762, filed on Jun. 16, 1998, now Pat. No. 6,493,427.

(51) Int. Cl.
*G06Q 50/00* (2006.01)
(52) U.S. Cl. .................... 705/2; 705/3; 705/4
(58) Field of Classification Search ............ 705/2, 705/3, 4; 700/216
See application file for complete search history.

(56) References Cited

U.S. PATENT DOCUMENTS

| | | | | |
|---|---|---|---|---|
| 4,436,962 | A | 3/1984 | Davis et al. | 179/18 |
| 4,766,542 | A * | 8/1988 | Pilarczyk | 705/3 |
| 4,958,280 | A | 9/1990 | Pauly et al. | 364/403 |
| 4,975,841 | A | 12/1990 | Kehnemuyi et al. | 364/401 |
| 5,208,762 | A * | 5/1993 | Charhut et al. | 700/216 |

(Continued)

FOREIGN PATENT DOCUMENTS

WO  WO 01/91105 A2  11/2001

(Continued)

OTHER PUBLICATIONS

Refill TeleManager, Logicon, 1996.

(Continued)

*Primary Examiner*—James A Kramer
*Assistant Examiner*—Martin A Gottschalk
(74) *Attorney, Agent, or Firm*—McCarter & English, LLP

(57) ABSTRACT

A central station is provided to which the pharmacy can forward calls at the convenience of the pharmacy. A caller will call in to the pharmacy to request a refill and the call will be automatically routed to the central facility unbeknownst to the caller. The central station will obtain the refill information required, preferably by means of an automated computer system as is known in the art. This information can then be transferred to the pharmacist in a number of ways, such as by periodically faxing the information to the pharmacy. Voice messages could be flagged and the pharmacist would have to call into the central facility to obtain the voice mail message. Alternatively, a PC could be installed in the pharmacy having a reduced version of a complete, stand-alone program. The refill information can then be sent to the pharmacy by modem and the pharmacist could see a computer display of the refill orders and could hear voice messages. Alternatively, the information could be e-mailed to the pharmacy. Finally, a pager system may be utilized to alert the pharmacist to retrieve orders by telephone with a password. It should also be noted that orders could be taken by the central station over the Internet rather than merely through customer calls. The central station can communicate with a pharmacy management service to obtain prescription refill authorization.

11 Claims, 11 Drawing Sheets

U.S. PATENT DOCUMENTS

| | | | |
|---|---|---|---|
| 5,249,221 A | 9/1993 | Ketring | 379/214 |
| 5,327,341 A | 7/1994 | Whalen et al. | 364/413.01 |
| 5,428,670 A | 6/1995 | Gregorek et al. | 379/67 |
| 5,444,767 A | 8/1995 | Goetcheus et al. | 379/67 |
| 5,450,488 A | 9/1995 | Pugaczewski et al. | 379/67 |
| 5,475,742 A | 12/1995 | Gilbert | 379/106 |
| 5,509,064 A | 4/1996 | Welner et al. | 379/265 |
| 5,511,594 A | 4/1996 | Brennan et al. | 141/98 |
| 5,597,995 A | 1/1997 | Williams et al. | 235/375 |
| 5,612,869 A | 3/1997 | Letzt et al. | 395/203 |
| 5,636,209 A | 6/1997 | Perlman | 370/281 |
| 5,646,912 A | 7/1997 | Cousin | 368/10 |
| 5,666,492 A | 9/1997 | Rhodes et al. | 705/3 |
| 5,737,396 A | 4/1998 | Garcia | 379/88 |
| 5,737,539 A | 4/1998 | Edelson et al. | |
| 5,772,585 A | 6/1998 | Lavin et al. | 600/300 |
| 5,825,856 A | 10/1998 | Porter et al. | 379/93.12 |
| 5,845,255 A | 12/1998 | Mayaud | 705/3 |
| 5,907,493 A | 5/1999 | Boyer et al. | 364/479.01 |
| 5,909,670 A | 6/1999 | Trader et al. | 705/14 |
| 5,926,526 A | 7/1999 | Rapaport et al. | 379/88.25 |
| 5,950,630 A | 9/1999 | Portwood et al. | 128/897 |
| 5,950,632 A * | 9/1999 | Reber et al. | 128/898 |
| 5,970,124 A | 10/1999 | Csaszar et al. | |
| 5,970,462 A | 10/1999 | Reichert | 705/2 |
| 5,971,594 A | 10/1999 | Sahai et al. | 364/479.12 |
| 5,982,863 A | 11/1999 | Smiley et al. | 379/112 |
| 5,996,006 A | 11/1999 | Speicher | |
| 6,014,631 A | 1/2000 | Teagarden et al. | 705/3 |
| 6,018,713 A | 1/2000 | Coli et al. | |
| 6,055,513 A | 4/2000 | Katz et al. | |
| 6,061,347 A | 5/2000 | Hollatz et al. | |
| 6,088,429 A | 7/2000 | Garcia | 379/88.22 |
| 6,108,634 A | 8/2000 | Podnar et al. | 705/2 |
| 6,112,182 A | 8/2000 | Akers et al. | 705/2 |
| 6,161,095 A | 12/2000 | Brown | 705/2 |
| 6,192,112 B1 | 2/2001 | Rapaport et al. | 379/88.22 |
| 6,202,923 B1 | 3/2001 | Boyer et al. | |
| 6,240,394 B1 | 5/2001 | Uecker et al. | 705/3 |
| 6,298,330 B1 | 10/2001 | Gardenswartz et al. | |
| 6,314,402 B1 | 11/2001 | Monaco et al. | 704/275 |
| 6,421,427 B1 | 7/2002 | Hill et al. | 379/88.14 |
| 6,456,699 B1 | 9/2002 | Burg et al. | 379/88.17 |
| 6,493,427 B1 | 12/2002 | Kobylevsky et al. | 379/67.1 |
| 6,578,003 B1 | 6/2003 | Camarda et al. | |
| 6,680,999 B1 | 1/2004 | Garcia | 379/88.22 |
| 6,718,017 B1 | 4/2004 | Price et al. | 379/88.22 |
| 6,744,862 B2 | 6/2004 | Kobylevsky et al. | 379/88.16 |
| 6,754,636 B1 | 6/2004 | Walker et al. | 705/26 |
| 6,768,788 B1 | 7/2004 | Langseth et al. | 379/67.1 |
| 6,804,654 B2 | 10/2004 | Kobylevsky et al. | 704/275 |
| 6,850,603 B1 | 2/2005 | Eberle et al. | 379/88.16 |
| 6,973,435 B1 | 12/2005 | Sioufi et al. | 705/2 |
| 7,058,584 B2 | 6/2006 | Kosiniski et al. | 705/2 |
| 7,267,278 B2 | 9/2007 | Lammle | |
| 7,558,380 B2 | 7/2009 | DiVenuta et al. | |
| 2001/0012335 A1 | 8/2001 | Kaufman et al. | 379/67.1 |
| 2002/0007285 A1 | 1/2002 | Rappaport | 705/2 |
| 2002/0010584 A1 | 1/2002 | Schultz et al. | |
| 2002/0023230 A1 | 2/2002 | Bolnick et al. | 713/202 |
| 2002/0048349 A1 | 4/2002 | Bixler et al. | 379/67.1 |
| 2002/0052760 A1 | 5/2002 | Munoz et al. | 705/2 |
| 2002/0091566 A1 | 7/2002 | Siegel | 705/14 |
| 2002/0143579 A1 | 10/2002 | Docherty et al. | 705/2 |
| 2002/0164004 A1 | 11/2002 | Tamura et al. | |
| 2003/0018495 A1 | 1/2003 | Sussman | 705/2 |
| 2003/0050799 A1 | 3/2003 | Jay et al. | 705/2 |
| 2003/0154106 A1 | 8/2003 | Marks | 705/2 |
| 2003/0216831 A1 | 11/2003 | Hart et al. | 700/235 |
| 2003/0225595 A1 | 12/2003 | Helmus et al. | 705/2 |
| 2003/0236729 A1 | 12/2003 | Epstein et al. | 705/36 |
| 2004/0019502 A1 | 1/2004 | Leaman et al. | 705/2 |
| 2004/0019567 A1 | 1/2004 | Herceg et al. | 705/64 |
| 2004/0107117 A1 | 6/2004 | Denny | 705/2 |
| 2004/0122712 A1 | 6/2004 | Hill, Sr. et al. | 705/2 |
| 2004/0172295 A1 | 9/2004 | Dahlin et al. | 705/2 |
| 2004/0228457 A1 | 11/2004 | Espejo et al. | 379/88.01 |
| 2005/0060200 A1 | 3/2005 | Kobylevsky et al. | |
| 2005/0069103 A1 | 3/2005 | DiVenuta et al. | 379/88.18 |
| 2005/0080651 A1 | 4/2005 | Morrison et al. | 705/2 |
| 2005/0209879 A1 | 9/2005 | Chalmers | 705/2 |
| 2006/0149587 A1 | 7/2006 | Hill, Sr. et al. | 705/2 |
| 2006/0247968 A1 | 11/2006 | Kadry | |
| 2006/0271398 A1 | 11/2006 | Belcastro | |
| 2007/0119930 A1 | 5/2007 | Jordan | |
| 2007/0219822 A1 | 9/2007 | Godwin et al. | |
| 2008/0208628 A1 | 8/2008 | Kobylevsky et al. | |
| 2008/0208986 A1 | 8/2008 | Kobylevsky et al. | |

FOREIGN PATENT DOCUMENTS

| | | | |
|---|---|---|---|
| WO | WO 03/069597 A1 | 8/2003 | |
| WO | WO 2006/031983 A2 | 3/2006 | |

OTHER PUBLICATIONS

Chopra, et al., "Voice-Activated Networked Workstation for a Physically Disabled Physician," Proceedings of the 16th Annual Int'l Conf. of the IEEE, Nov. 3-6, 1994.

PCT International Search Report mailed Feb. 23, 2007, in connection with International Publication No. WO 2006/031983 A2 (3 pages).

PCT Written Opinion mailed Feb. 23, 2007, in connection with International Publication No. WO 2006/031983 A2 (3 pages).

PCT International Preliminary Examination Report mailed Mar. 20, 2007, in connection with International Publication No. WO 2006/031983 A2 (4 pages).

PCT International Search Report mailed Jul. 11, 2003, in connection with International Publication No. WO 03/069597 A1 (4 pages).

Press Release entitled "Harland Financial Solutions and Maxxar Corporation Establish Alliance to Bring One-to-One Marketing to Telephone Banking," dated Jan. 9, 2001 by Harland Financial Solutions (2 pages).

Brochure entitled "Customer Capture—CTG Implements a Customer-Specific Marketing Program for a Major Retailer," dated Sep. 2003 by CTG (2 pages).

Brochure entitled "TeleVoice—The Next Generation of Voice Response for Mortgage Servicing Call Centers," dated Mar. 2006 by Fidelity National Information Services (6 pages).

"Case Studies—Client: State of Michigan Office of Retirement Services," website printout from http:/www.covansys.com/clients/case_michigan.htm, dated Apr. 13, 2006 (4 pages).

Notice of Allowance dated Aug. 16, 2002, from U.S. Patent No. 6,493,427 (5 pages).

Interview Summary dated May 31, 2002, from U.S. Patent No. 6,493,427 (3 pages).

Office Action dated Apr. 12, 2002, from U.S. Patent No. 6,493,427 (9 pages).

Office Action dated Oct. 22, 2001, from U.S. Patent No. 6,493,427 (27 pages).

Advisory Action dated May 23, 2001, from U.S. Patent No. 6,493,427 (4 pages).

Office Action dated Jan. 31, 2001, from U.S. Patent No. 6,493,427 (15 pages).

Office Action dated May 22, 2000, from U.S. Patent No. 6,493,427 (19 pages).

Supplemental Notice of Allowability dated May 4, 2004, from U.S. Patent No. 6,744,862 (5 pages).

Notice of Allowance dated Jan. 13, 2004, from U.S. Patent No. 6,744,862 (6 pages).

Office Action dated Oct. 3, 2003, from U.S. Patent No. 6,744,862 (10 pages).

Response to Rule 312 Communication dated Aug. 25, 2004, from U.S. Patent No. 6,804,654 (3 pages).

Notice of Allowance dated Jun. 28, 2004, from U.S. Patent No. 6,804,654 (4 pages).

Inteview Summary dated Mar. 10, 2004, from U.S. Patent No. 6,804,654 (4 pages).
Office Action dated Dec. 18, 2003, from U.S. Patent No. 6,804,654 (11 pages).
Office Action dated Jun. 16, 2003, from U.S. Patent No. 6,804,654 (10 pages).
Office Action dated Jun. 11, 2008, from pending U.S. Appl. No. 10/672,556 (13 pages).
Office Action dated Feb. 5, 2008, from pending U.S. Appl. No. 10/672,556 (13 pages).
Office Action dated Nov. 5, 2008, from issued U.S. Patent No. 7,558,380 (12 pages).
Notice of Allowance dated Mar. 6, 2009, from issued U.S. Patent No. 7,558,380 (9 pages).
International Search Report of the International Searching Authority mailed May 5, 2009, issued in connection with International Patent Appln. No. PCT/US09/37948 (3 pages).
Written Opinion of the International Searching Authority mailed May 5, 2009, issued in connection with International Patent Appln. No. PCT/US09/37948 (5 pages).
Press release dated 1999 and entitled "Hannaford Bros. Installs Refill Telemanger IVR System," (1 page).
Printout dated Oct. 31, 2001, entitled: "Refill Telemanager—The Affordable Automation Tool for Prescription Refills," (http://www.telemanager.com/RTInfo/RTInfo.html) (3 pages).
"2008 Buyers Guide Quick Reference Table," ComputerTalk Magazine, Mar./Apr. 2008, p. 85 (1 page).
"TeleManager Technologies, Inc.—The New Prescription for All Your Telecommunication Needs," ComputerTalk, (2008) p. 42 (1 page).
Brochure, "Refill Telemanager In-Store IVR System," (2007) (1 page).
Brochure, "Telemanager On-Demand IVR System," (2007) (1 page).
Brochure, "NEW Community Pharmacy Automated Refill Telephone System," (1992) (2 pages).
"Quick Reference Guide," (1992) (1 page).
Brochure, "Refill Telemanager—The Affordable Automation Tool for Prescription Refills," (1990) (2 pages).
"Refill Telemanager User's Guide," (2009) (58 pages).
"Refill Telemanager User's Guide," (1997) (37 pages).
Brochure, "Refill Telemanager Service," (1998) (2 pages).
Brochure, "Refill Telemanager Service—Frequently Asked Questions," (1998) (1 page).
Brochure, "Finally! Unique, New Technology Designed to Increase Your Sales, Customer Service, and Employee Productivity at a Price Every Store Can Afford!," (1998) (1 page).
Brochure, "Refill Telemanager Service—Information Retrieval Guide" (1998) (2 pages).
Brochure, "Refill Telemanager Service" (1998) (2 pages).
Office Action dated Jun. 8, 2010, from pending U.S. Appl. No. 11/711,496 (17 pages).
Cain, et al., "Health e-People: The Online Consumer Experience," Aug. 2000, Institute for the Future (73 pages).
"Micolog Expands Services for the Retail Pharmacy Market," PR Newswire, Aug. 22, 1997 (1 page).
"Dial-a-Script Saves Bi-Mart Money and Time," Drug Store News, vol. 22, Issue 12, Aug. 28, 2000 (1 page).
Popolillo, "Shopko, ateb Team Up for Pharmacy Convenience," Drug Store News, vol. 21, Issue 4, Mar. 1, 1999 (2 pages).
Frederick, "Wal-Mart's New Combo Format Drawing Pharmacy, Food Customers," Drug Store News, Nov. 23, 1998 (3 pages).
Frederick, "American Drug Stores," Drug Store News, vol. 18, Issue 7, Apr. 29, 1996 (3 pages).
"Shopko Sees Health Cam as Corn Part of Operation," Chain Drug Review, No. 14, vol. 21, Aug. 30, 1999 (2 pages).
"CVS Uses Technology to Change the Face of its Pharmacy Business; RX: Marketplace," Chain Drug Review, No. 21, vol. 19, Dec. 15, 1997 (2 pages).
"Longs Drugs Rolling Out Novadigm to 380+ Remote Stores to Deploy and Manage Its Core Business Applications," PR Newswire, Aug. 23, 1999 (2 pages).
"Microlog Completes Systems Integration Work for Eckerd Pharmacy Chain Equities," PR Newswire, Jul. 21, 1999 (2 pages).
"Getting the Message; How Protodigm and Pharmacia & Upjohn Use Communications Systems," Pharmaceutical Times, Jul. 31, 1998 (1 page).
"Synectics Inks IRV Pact With Wal-Martannotated Title-Wal-Mart Pharmacies Will Use an Interactive Voice Response System Developed by Synectics, Inc. (Raleigh, NC) to Give Customers and Doctors 24-Hour Access to the Pharmacy," Drug Store News, vol. 19, Issue 17, Oct. 20, 1997 (3 pages).
"Touch Tone Prescriptions: Telephony and Beyond," Pharmacy Times, vol. 63, 1997 (2 pages).
Thompson, "Expanding Role of Certified Pharmacy Technicians in Outpatient Pharmacy Automation Management," ASHP Midyear Clinical Meeting, vol. 32, Dec. 1997 (1 page).
"ATEB Installs Pharmacy Line Voice Response System at ShopKo Stores," Drug Store News, vol. 20, Issue 13, Aug. 24, 1998 (1 page).
Pastore, "Voice System Reins in Agency's Costs," Computerworld, Sep. 17, 1990 (2 pages).
SOAP Version 1.2 Part 1: Messaging Framework (Second Edition), http://www.w3.org/TR/soap12-part1/, Apr. 27, 2007 (47 pages).
Office Action dated Sep. 29, 2009, from pending U.S. Appl. No. 10/641,307 (10 pages).
Office Action dated Jan. 14, 2010, received from the Canadian Patent Office, in connection with pending Canadian Application No. 2,475,959 (4 pages).
Office Action dated May 25, 2010, from pending U.S. Appl. No. 10/941,307 (12 pages).
Office Action dated Oct. 1, 2010, from pending U.S. Appl. No. 12/058,931 (13 pages).
Interview Summary dated Sep. 13, 2010, from pending U.S. Appl. No. 10/941,307 (6 pages).

* cited by examiner

| | Name | Text | | |
|---|---|---|---|---|
| ▶ | Initial Greeting | You have reached Refill Telemanager Demonstration Line | | Edit |
| ☐ | General Announcement | We are open 7 days a week | | Exit |
| ☐ | After-Hours Announcement | If this is an emergency | | |

Announcement

FIG. 6

| Special Holidays | | | | | | |
|---|---|---|---|---|---|---|
| Washington's Birthday | 02/21 | 02/20 | 02/19 | 02/18 | 02/17 | Add |
| Name | 1998 | 1999 | 2000 | 2001 | 2002 | Edit |
| New Year's Day | 01/01 | 01/01 | 01/01 | 01/01 | 01/01 | |
| Martin Luther King Day | 01/19 | 01/18 | 01/17 | 01/15 | 01/21 | Delete |
| Lincoln's Birthday | 2/121 | 02/12 | 02/12 | 02/12 | 02/12 | |
| ▶ Washington's Birthday | 02/21 | 02/20 | 02/19 | 02/18 | 02/17 | Exit |
| Memorial Day | 05/25 | 05/31 | 05/29 | 05/28 | 05/27 | |
| Independence Day | 07/04 | 07/04 | 07/04 | 07/04 | 07/04 | |
| Labor Day | 09/07 | 09/06 | 09/04 | 09/03 | 09/02 | |
| Columbus Day | 10/12 | 10/11 | 10/09 | 10/08 | 10/14 | |
| Veterans' Day | 11/11 | 11/11 | 11/11 | 11/11 | 11/11 | |
| Thanksgiving Day | 11/26 | 11/25 | 11/23 | 11/22 | 11/28 | |
| Christmas Day | 12/25 | 12/25 | 12/25 | 12/25 | 12/25 | |
| Election Day | 11/03 | 11/02 | 11/07 | 11/06 | 11/05 | |

FIG. 7

Schedule

WeekDays

| | Name | Pickup | Delivery |
|---|---|---|---|
| | Sunday | 09:00am-09:00pm | 11:00am-09:00pm |
| | Monday | 09:00am-09:00pm | 11:00am-09:00pm |
| ▶ | Tuesday | 09:00am-09:00pm | 11:00am-09:00pm |
| | Wednesday | 09:00am-09:00pm | 11:00am-09:00pm |
| | Thursday | | |
| | Friday | 09:00am-09:00pm | 11:00am-09:00pm |
| | Saturday | 09:00am-09:00pm | 11:00am-09:00pm |

Holidays

| | Name | Pickup | Delivery |
|---|---|---|---|
| ▶ ☐ | New Year's Day | 09:00am-09:00pm | 11:00am-09:00pm |
| ☐ | Martin Luther King Day | 09:00am-09:00pm | 11:00am-09:00pm |
| ☐ | Lincoln's Birthday | 09:00am-09:00pm | |
| ☐ | Washington's Birthday | 09:00am-09:00pm | |
| ☐ | Memorial Day | | 11:00am-09:00pm |
| ☐ | Independence Day | 09:00am-09:00pm | 11:00am-09:00pm |
| ☐ | Labor Day | 09:00am-09:00pm | 11:00am-09:00pm |
| ☐ | Columbus Day | 09:00am-09:00pm | 11:00am-09:00pm |
| ☐ | Veterans' Day | 09:00am-09:00pm | 11:00am-09:00pm |
| ☐ | Thanksgiving Day | 09:00am-09:00pm | 11:00am-09:00pm |
| ☐ | Christmas Day | 09:00am-09:00pm | 11:00am-09:00pm |
| ☐ | Election Day | 09:00am-09:00pm | 11:00am-09:00pm |

Tuesday Pickup

Time: 09:00am-09:00pm
Interval: 2.0

| Start Hour | End Hour | Interval |
|---|---|---|
| 09:00am | 09:00pm | 2.0 |

Add  Delete  Apply

| | Call Time | Telephone # | Type | Time Due | Voice | Status |
|---|---|---|---|---|---|---|
| 90009 | 05/06 06:03pm | | Incomp | 05/06 08:00pm | | Filled |
| 90007 | 05/06 05:58pm | | Incomp | 05/06 07:45pm | | Filled |
| 90006 | 05/06 05:56pm | | Incomp | 05/06 07:45pm | | Filled |
| 90003 | 05/06 05:51pm | | Incomp | 05/06 07:45pm | | |
| 90002 | 05/06 05:49pm | | Incomp | 05/06 07:45pm | | Filled |
| 90002 | 05/06 05:47pm | | Incomp | 05/06 07:00pm | | |
| 90001 | 05/06 05:05pm | (732) 444-4444 | Pickup | 05/06 07:00pm | | Filled |
| 45632 | 05/06 05:00pm | | Incomp | 05/06 05:45pm | | |
| 74568 | 05/06 03:57pm | (732) 111-1111 | Pickup | 05/06 05:00pm | Yes | Filled |
| 11111 | 05/06 03:07pm | (732) 707-0608 | Incomp | 05/06 05:00pm | Yes | |
| 70008 | 05/06 03:05pm | (732) 705-0607 | Incomp | 05/06 05:00pm | | Filled |
| 70007 | 05/06 03:03pm | (732) 703-0606 | Incomp | 05/06 05:00pm | | |
| 70006 | 05/06 03:02pm | (732) 702-0605 | Incomp | 05/06 04:45pm | | Filled |
| 70005 | 05/06 02:59pm | | Incomp | 05/06 04:45pm | | Filled |
| 70004 | 05/06 02:58pm | (732) 555-5555 | Pickup | 05/06 11:00am | | Filled |
| 70003 | 05/06 09:09am | (732) 444-4444 | Delivery | 05/06 11:00am | | |
| 66666 | 05/06 02:50am | (732) 333-3333 | Incomp | 05/05 4:45pm | | |
| 44444 | 05/05 2:49pm | (732) 222-2222 | Pickup | 05/05 4:45pm | Yes | Filled |
| 33333 | 05/05 2:46pm | (732) 111-1111 | Delivery | 05/06 11:00am | | Filled |
| 22222 | 05/06 02:37am | | | | | |
| 11111 | | | | | | |

Calls Today:0   Refills Today:0   Doctors Today:0   Messages Today:0   Unfilled:11   11:59AM

REMOTE PRESCRIPTION REFILL SYSTEM

RELATED APPLICATION

This application is a continuation-in-part application of U.S. patent application Ser. No. 09/097,762, filed Jun. 16, 1998 by Kobylevsky, et al., entitled Remote Prescription Refill System, now U.S. Pat. No. 6,493,427, the entire disclosure of which is expressly incorporated herein by reference.

BACKGROUND OF THE INVENTION

1. Field of the Invention

This invention relates generally to a remote refill prescription system for automatically handling prescription re-fill orders for pharmacies. More specifically, this invention relates to a remote prescription refill system, wherein refill orders are directed to a central location or central station, which confirms refill availability electronically with a pharmacy management system, and then the refill information is transferred by one or more of various ways to the pharmacy.

2. Related Art

Traditionally, prescription refills were ordered by visiting a pharmacy and requesting a refill. Eventually, one could obtain a prescription refill by telephoning the pharmacy and speaking with the pharmacist to request the refill. However, this could take up a large amount of a pharmacist's time. In a busy pharmacy, numerous telephone requests for refills could prevent the pharmacist from actually performing his or her work—preparing drugs.

Accordingly, what was developed, and are now in widespread use, are automated telephone prescription refill systems which handle incoming calls, obtain the prescription refill request and provide the request to the pharmacist. Many of these systems are computer-based and run sophisticated software programs. Such systems may include microprocessors, memory, monitors, modems, printers, and may even require technical support. Such systems can be expensive, and though affordable by large, busy pharmacies, or pharmacy chains, these systems may not be affordable for every pharmacy. Such a "stand-alone" system is discussed, hereinafter, in the Detailed Description of the Invention.

Accordingly, what is desired, and has not heretofore been provided, is an inexpensive automated system for pharmacies for handling prescription refill orders. Additionally, it is desired that such a system can be utilized by pharmacists with varying technical capabilities without the need for technical support. Still further, it would be desirable to provide such a system remote from a pharmacy and to provide the system with the capability to confirm prescription refill availability by electronic communication with a pharmacy management system.

Past efforts in this general area include the following:

Rhodes, et al., U.S. Pat. No. 5,666,492 discloses a computer based pharmaceutical care cognitive services management system and method that facilitates the transformation of a vendor to a health care provider. The invention captures the value added by a pharmacist to a patient encounter and enables the pharmacist to financially recover for the services provided. The system allows for the processing of interruptions during sessions.

Brennan et al., U.S. Pat. No. 5,511,594 discloses a modular pharmacy system that can be standardized for efficient arrangement of successive steps in the preparation of prescriptions. The pharmacy system includes a plurality of workstations for completing successive steps in the admixture of intravenous solutions and drugs.

Gilbert, U.S. Pat. No. 5,475,742 discloses a system for remote data collection. The data is then sent to a central site via a telephone network to store the data for processing by a central processing unit. The invention has particular applicability in the collection and processing of data for statistical purposes in the field of pharmacological distribution.

Pugaczewski, et al., U.S. Pat. No. 5,450,488 discloses a centralized, multiple-service voice messaging system. The system permits differentiation between incoming calls. Additional directory numbers are dedicated to message service systems. The central office forwards calls dialed to the dedicated directory numbers to the voice mail system, which recognizes the numbers and performs services based on the directory number dialed.

Kehnemuyi, et al., U.S. Pat. No. 4,975,841 discloses a method and apparatus for automatically contacting customers and reporting order status data. Memory is provided for receiving and storing the customer order status information including product order information, scheduled and actual shipping dates and the customer's telephone number. A telephone dialer is provided for dialing customer telephone numbers. The telephone dialer sequentially dials customer's telephone numbers and a corresponding customer report facsimile is automatically transmitted to the customer.

Pauly, et al., U.S. Pat. No. 4,958,280 discloses an apparatus and method for filing prescriptions for disposable contact lenses. Eye care professionals may place automated orders through personal computers or by direct telephone calls. A central station having a variety of file storage means, which maintains the files, and selectively processes the files in accordance with its operations. Orders are processed in a batch mode and order forms may be printed. The order forms are then delivered to the inventory-distribution area where orders are verified, packaged and shipped to the customer. At the time of the receipt of the order, and at shipping, appropriate inventory file adjustments are made.

Pilarczvk, U.S. Pat. No. 4,766,542 discloses a system for contacting pharmacy customers to automatically remind them that their prescriptions need to be refilled. The system includes a computer, memory, and automatic telephone dialing and voice synthesizing equipment. A printed report is provided to the pharmacist.

Some additional patents that pertain to this field include Perlman, U.S. Pat. No. 5,636,209, which discloses a modem for supporting multiple site call conference data communications; Williams, et al., U.S. Pat. No. 5,597,995, which discloses an automated medical prescription fulfillment system having work stations for imaging, filing and checking the dispensed drug or product; Whalen, et al., U.S. Pat. No. 5,327,341, which discloses a computerized file maintenance system for managing medical records including narrative reports; Ketring, U.S. Pat. No. 5,249,221, which discloses a telephone answering system with call transfer; and Davis et al., U.S. Pat. No. 4,436,962, which discloses a call cover arrangement wherein a covered call is redirected sequentially to each of the covering stations in a coverage group in an order of preference until the call is answered or abandoned.

OBJECTS AND SUMMARY OF THE INVENTION

It is a primary object of this invention to provide a prescription refill system having a central station, which automatically processes pharmacy prescription refills.

It is another object of the present invention to provide a prescription refill system where a caller will telephone a pharmacy and be automatically routed to a central station where the refill information will be obtained.

It is an additional object of the present invention to provide a prescription refill system where the refill information from the central station can be transferred to the pharmacy in a variety of ways.

It is even an additional object of the present invention to provide a system of the class described where the refill information is transmitted to the pharmacy by facsimile transmission.

It is still even an additional object of the present invention to provide a system where the refill information is transmitted to the pharmacy by e-mail.

It is still a further object of the present invention to provide a prescription refill system where the refill information is transmitted to the pharmacy over the Internet.

It is even a further object of the present invention to provide a system where the pharmacist can access voice mail information left by callers on the central station.

It is yet another object of the present invention to provide a system where the pharmacies can receive order information from the central station by the use of the telephone with a password.

It is even another object of the present invention to provide a system where the pharmacist can use a local personal computer (PC) to access refill order information and voice messages from the central station.

It is still a further object of this invention to provide a prescription refill system utilizing a central station which is transparent to the refill requestor, i.e., people requesting refills perceive themselves to be dealing directly with the pharmacy.

It is even a further object of the present invention to provide a remote prescription refill system wherein the central station receiving prescription refill requests can electronically communicate directly with a pharmacy management system to confirm prescription refill availability.

A central station is provided to which the pharmacy can forward calls at the convenience of the pharmacy. A caller will call in to the pharmacy to request a refill and the call will be automatically routed to the central facility unbeknownst to the caller. The central station will obtain the refill information required, preferably by means of an automated computer system. This information can then be transferred to the pharmacist in a number of ways, such as by periodically faxing the information to the pharmacy. Voice messages could be flagged and the pharmacist would call into the central facility to obtain the voice mail message. Alternatively, a PC could be installed in the pharmacy having a reduced version of a complete, stand-alone program. The refill information can then be sent to the pharmacy by modem and the pharmacist could see a computer display of the refill orders and could hear voice messages. Alternatively, the information could be e-mailed to the pharmacy. Finally, a pager system may be utilized to alert the pharmacist to retrieve orders by telephone with a password. It should also be noted that orders could be taken by the central station over the Internet rather than merely through customer calls. The central station receiving prescription refill requests can electronically communicate directly with a pharmacy management system to confirm prescription refill availability.

BRIEF DESCRIPTION OF THE DRAWINGS

Other important objects and features of the invention will be apparent from the following Detailed Description of the Invention taken in connection with the accompanying drawings in which:

FIG. 6 is a is a computer display of Holidays for scheduling for the invention.

FIG. 7 is a computer display of the pickup and delivery schedule for the invention.

FIG. 8 is a computer display of refill orders generated on a PC at the pharmacy in accordance with one embodiment of the invention.

DETAILED DESCRIPTION OF THE INVENTION

Figure 1:
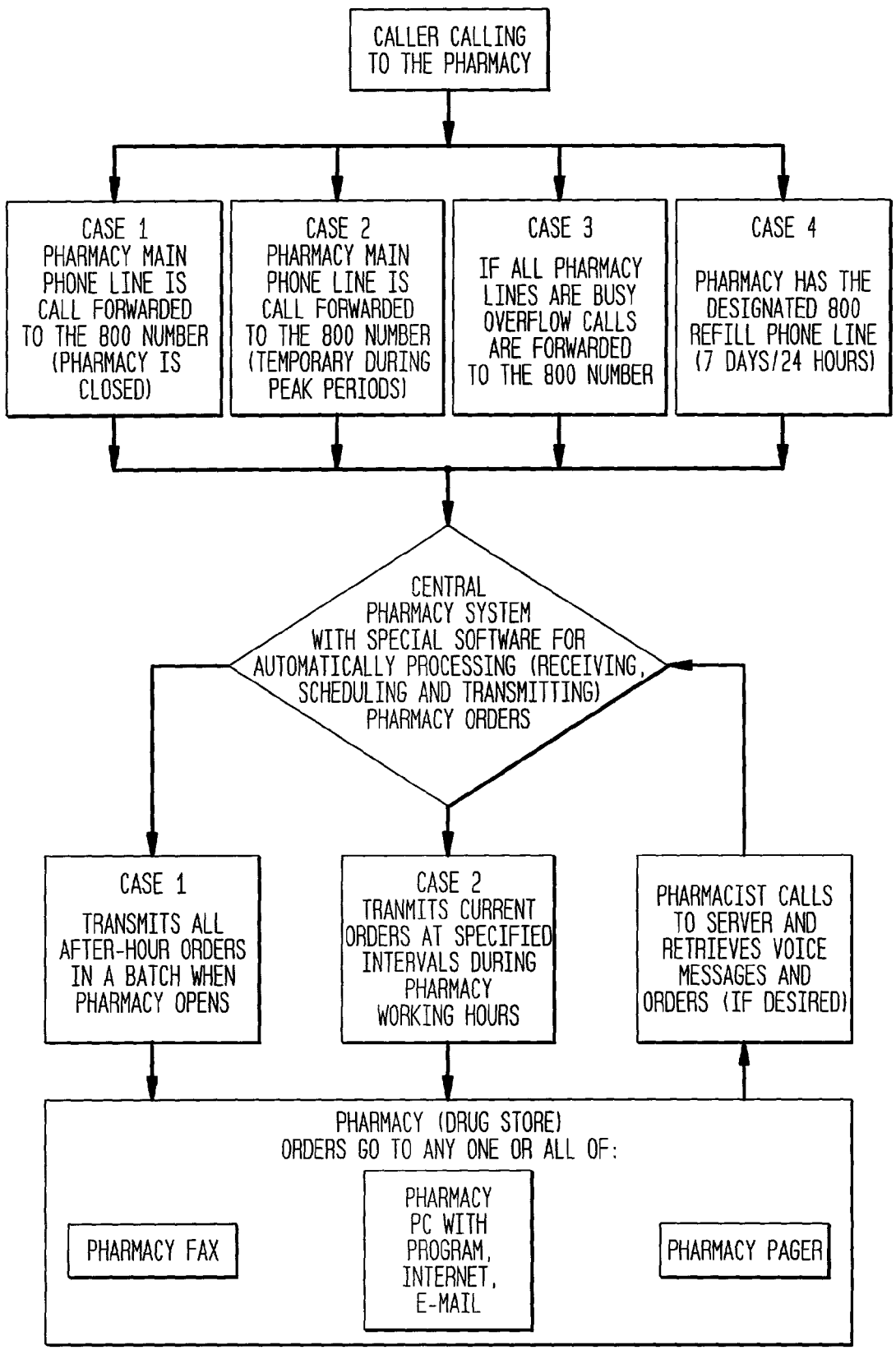
FIG. 1 is a flow chart showing the operation of the invention.

In discussing the present invention, it is useful to begin with a discussion of the assignee's commercially available stand-alone refill prescription system which has many programming similarities with the present invention. In the stand-alone system, the computer programs are located at the pharmacy.

Before starting to use the stand-alone system, it has to be customized by entering all the necessary information about the business and choosing the optional features. This is known as the setup process. It is important to check the computer's date and time settings and to correct them before starting. To start the stand-alone system, one must turn the power on to start the computer, on the Windows® desktop screen click on the start button, click on Programs and then click on the program icon, when the program starts, it displays the title screen briefly and then the main program screen appears.

To access the Setup screen click on File -Setup. The main Setup screen will be displayed. As a security precaution a password should be used. To insert a password: Click on the Change Password button. The Change Password window appears.

In the Change Password window type the password of four characters in the New Password box. Press the TAB key to move to the Confirm Password box and retype the password exactly as before. Click OK. This returns to the main Setup window. The Password takes effect the next time Setup is started.

The pharmacy name is entered in the main Setup window. There is also an option to record the name of the pharmacy for use in Outbound Call modules (if it has not yet been prerecorded). To record the pharmacy name, turn on the microphone. Type the name of the pharmacy into the Name of Pharmacy text box. Click on the Record button in the main Setup window and the Record Pharmacy Name window will be displayed. Click on the Record button and speak into the microphone. The blinking word "Recording" instead of "Stopped" and the movement of a slider will show the progress of recording. Click on the Stop button when finished recording. Click on the Play button to hear the recording. In the Script window, the text as recorded may be entered for future reference. Click OK to return to the main Setup window.

To import an existing voice file for the Pharmacy Name, from the Record Pharmacy Name window click on the Import button. A standard Windows 95 Open screen will be displayed. Select the file to be imported as the Pharmacy Name and click on the Open button. In the Script window, the user has the option to type in the text of the voice file, which was imported for future reference. Click OK to return to the main Setup window.

The Initial Announcement is the first announcement customers hear when they access the program. It is required that at least one initial announcement always be present. The General Announcement is an optional feature that may provide callers with general information about the pharmacy (e.g., hours, directions, promotional and sale information, etc.) The after-hours Announcements is an optional feature that will be only played when the pharmacy is closed and provide callers with information regarding the nearest 24 hour store or any other after-hours emergency related information if a caller chooses to listen to it from the Main voice menu.

When customers call the pharmacy, the first thing they hear is an Initial Announcement (e.g., "You have reached the ABC Pharmacy"). The announcement may be recorded by the pharmacy staff or imported as a prerecorded voice file. To record the Initial Announcement, click on the Announcements button in the Setup window and the Announcements window will appear. Click on the tab Initial. Click on the Add button. This will bring up the Add Initial Announcement window. Type in a name to identify the announcement. One can record more than one initial announcement and save the inactive recordings for later use. Therefore, pick a name that will allow one to distinguish between them (e.g., "Standard," "Holiday," etc.) Type the text that will be record in the Script window for future reference. Click on the Record button. Push the Stop button when finished recording. Click on the Play button to hear the recording. Click OK when finished. This returns to the Announcements window.

Select the initial announcement for the program to use from the list of announcements. The initial announcement, whose name is highlighted and is shown in the Initial Announcement text box in the Announcements window, is the initial announcement that will be played by the system. Click OK. This returns to the main Setup window.

To import a prerecorded voice file for the Initial Announcement, from the Add Initial Announcement or the Edit Initial Announcement windows click on the Import button. A standard Windows 95 Open screen will be displayed. Select the file that will be imported as an initial announcement and click on the Open button. The selected file name will appear in the Name text box of the Add Initial Announcement window. In the Script window, type in the text of the imported initial announcement for future reference. Click OK when finished. This returns to the Announcements window. Select the initial announcement the program is to use from the list of announcements by clicking on it. The initial announcement, whose name is highlighted and is shown in the Initial Announcement text box, is the initial announcement that will be played by the system. If an initial announcement was not recorded words "Not Recorded" will appear in the Initial Announcement text box in red color.

One may also choose to make available to callers a General Announcement about the pharmacy. The process of recording a General Announcement is very similar to the process of recording an Initial Announcement. In the Announcements window click on the tab General. Check the General Information check box (by clicking in it) to activate it. Add, Edit and Delete buttons will become enabled. Click on the Add button. This will bring up the Add General Announcement window. The recording of the General Announcement is the same as the recording of the Initial Announcement. The procedure for importing prerecorded voice files for a General Announcement is the same as for an Initial Announcement.

One may also choose to activate an after-hours Announcement. The process of recording an after-hours Announcement is very similar to the process of recording an Initial Announcement. In the Announcements window click on the tab after-hours.

Check the after-hours Announcement check box (by clicking in it). The Add, Edit and Delete buttons will become enabled. Click on the Add button. This will bring up the Add after-hours Announcement window. Follow the stems for recording the Initial Announcement. The procedure for importing the prerecorded voice files for an after-hours Announcement is the same as for an Initial Announcement.

The Options window is a part of the Setup process where the program can be fully customized by choosing the main features that are essential for running in a particular business environment. There are only several settings in the Options that are required to be completed: the length of the customer's telephone number, the local area code and the length of the Rx number. The rest of the settings are optional.

To access the Options window, click on the Options button in the main Setup window and the Options window will be displayed. When selection of the options to be included in the system is completed, click OK to save the settings and return to the main Setup window or click Cancel to exit the Options window without saving the changes.

The program requests a customer's phone numbers in case they need to be reached. To choose the options in the Request Phone Number section, type the pharmacy local area code in the Local Area Code text box. Click on the Seven Digits radial button if the pharmacy services a local region with only one area code and it is not desired to request an area code with the customer's phone number. Click on the Ten Digits radial button if the pharmacy services customers from more than one area code region and it is desired that the program request an area code with the customer's phone number.

If the program is integrated with an existing Pharmacy Management System it will request customer's phone numbers only in the cases where the number detected by Caller ID does not match any phone number in the customer's profile file.

The program allows customers to leave the refill voice message attached to their refill order (for example: "I don't have a refill number handy but I need another refill of XYZ you have on file to be delivered with my order." or "Please contact my doctor at 212-222-2222 for refill authorization, of XYZ." or "Add to my delivery order 100 ABC pills and three tubes of Crest® regular toothpaste.") If this option is chosen the system will prompt the callers during their refill request session to leave a voice message with instructions to the pharmacist. Check the Ask for Refill Message check box to activate this feature.

Voice Messaging allows customers to leave a voice message only, thus serving as an answering machine for all incoming voice lines. When activated, the system will prompt the caller on the Main Voice Menu to press a designated button on a telephone keypad if they want to leave a message. Check the Activate Voice Messaging check box to activate this feature.

When a new order is received, it is recommended that a sound from computer speakers is issued to immediately alert the pharmacist of a new order. Check the New Order—Sound Alert check box to activate this feature.

The Order Status Verification feature allows callers to verify the status of the prescription refill previously ordered through the program. If the option is activated, the customers will have the choice on the Main Voice Menu of checking the status of their refill order. Check the Order Status Verification check box to activate this feature.

The Doctor's Line Announcement is designed for pharmacies with multi-line telephone environment without call routing. The system recognizes doctors transferring to the pharmacy phones, either from the Doctor's Voice Menu or from bypassing the system by means of the direct transfer feature, and announces through the computer speakers the number of the phone line on which the doctor is holding. Check the Doctor's Line Announcement check box to enable this feature.

Customers may speak directly to the pharmacy staff. Some pharmacies may choose to have a dedicated telephone line solely for prescription refills and have a second number for direct calls to the pharmacy. When activated, the system will prompt the caller to press the zero key if they require personal assistance. Check the Allow Transfer to Pharmacy check box to activate this feature. Enter in the Dial String text box the dialing combination which controls the switching device (PBX, KSU, line switching box).

While entering refill numbers and/or recording voice messages callers will not be able to transfer their calls to the pharmacy using the zero key. In such cases and/or at any time during the call callers have the option to return to the Main Voice Menu by pressing the star key and then to be transferred to the pharmacy by pressing the zero key.

When the pharmacy is closed the system does not offer to callers the choice of transferring their calls to the pharmacy phones by pressing the zero key. However pharmacy staff and designated callers may transfer their after-hours calls to the pharmacy phones by pressing the nine ("9") key at any time during the Main Voice Menu. This option is never announced to general callers.

The First Choice feature allows one to change the order of playing the Refill and Doctor's prompts on the Main Voice Menu. One chooses which menu choice, Refill or Doctor, should be played first by checking the appropriate option in the First Choice section: Click on the Doctors radial button if callers are to hear the choice "Doctor's Office only" first on the Main Voice Menu. Click on the Cust. Refills radial button if callers are to hear the choice "To Refill a Prescription" first on the Main Voice Menu.

The Doctor's Orders section allows adjusting the Doctor's Menu to the preferences of doctors in the community. One may choose any combination of the following options by checking the appropriate check boxes in the Doctor's Orders section. The Refill option allows doctors to record new prescriptions and/or refill authorizations in just one recording. They are prompted by the system to state their full name and phone number, patient full name and phone number and all relevant information for the new prescription and/or refill authorization.

The Message option allows doctors to leave a message for the pharmacy staff. They are prompted by the system to leave their name, phone number and a detailed message. The Transfer option allows doctors to be immediately transferred to the pharmacy staff by pressing the zero key on the keypad of their phones. If none of these options is activated, the Doctor's Menu will be turned off and the choice of "Doctor's Office only" will not be offered on the Main Voice Menu. If only the Transfer is selected, then whenever doctors press the "Doctor's Office only" option on the Main Voice Menu they will be automatically transferred to the pharmacy staff. If a combination of any of the three options is activated, the doctor will hear the short menu offering the selected choices.

The program requires that the number of digits in the Rx Number used in the Pharmacy (any number between 3 and 10 excluding letters, preceding or succeeding if any) be specified. The program validates a customer's entry to make sure the correct number of digits have been punched in. If necessary (for example, if Rx numbers of two different length are used) one may choose a variable length for the Rx number by typing a "*" in the Length of Rx number text box. If variable length of the Rx number is chosen the system will prompt customers to follow the input of the Rx number by the "#" sign. In any case the system will play back to customers the entered Rx numbers for verification. Type the number of digits in the prescription refill number or a "*" for variable length in the Length of Rx number text box.

The program permits choice of the number of days' worth of orders (from 2 to 7 days) that will be stored in the system and displayed on the main screen. The fewer number of days are stored, the faster the system works. By default the system stores orders for 3 days. To change this number, click on the Days to Store text box and delete the existing number. Type in the desired number of days for storing orders in the system.

There are two different ways of printing orders in the program, Receipt Printing and Full-page Printing with receipt printing, all orders are printed automatically on the receipt (cash register type) printer in the form of order slip as soon as they are received. Click on the arrow in the Receipt Printer list and select the desired receipt printer from the drop-down choices to enable this feature. If no printing is required (for example, when the system is in integrated mode) choose option "No Printer." With full-page printing, the program can print in the full-page format on any printer connected to the computer and installed in the Windows® system. In full-page printing mode, orders sorted on the Main Screen may be printed in a variety of way (refills, filled, doctors' orders, messages, etc.) in full-page format.

The Terminal Integration, Terminal Emulation and Modem sections of the Options deal with the integration of the program with other Pharmacy Management Systems and some other applications. Each of them requires different special settings in the Integration, Terminal Emulation and Modem sections. These sections will be preset or will be configured by the authorized technician during the installation.

The program requires one to specify the holidays when the pharmacy is closed so that it will not schedule prescription refills on those days. Click on the Holidays button in the main Setup window and the Holidays window will be displayed. Click on the each specific holiday on the holiday's list to select the holidays during which the pharmacy will be closed for the whole day. Wvhen choosing a holiday on the list, it is highlighted in red, both on the list and on the corresponding day. If the pharmacy will be closed on a holiday that is not on the list, one may manually designate a day for this holiday by clicking on that day on the calendar (use the scroll bar under the calendar to find any day of the year). The program will display a dialog box to ask if one would like to designate this day as a holiday. Click OK. To remove the Holiday from the schedule, click on the name of the Holiday on the list or date of the Holiday on the calendar. The program will display a dialog box to ask if one would like to remove this holiday from the office calendar. Click OK. Click the Close button when done to save the settings and return to the main Setup window.

The phone ports part of the Setup deals with the configuration of telephony boards used in the computer as well as with actual layout of the telephone lines to the telephony boards ports. One may also choose which telephone lines are to be used for outbound calls to customers whose refill orders are ready but were not picked up, or to remind them that their medication is due to be refilled. Click on the Phone Ports button to display the Phone Ports Setup window. Select the first line to configure by clicking on the first row in the Phone Ports Setup window (the row pointer, a black arrow, will point to that row). Press the TAB key on the keyboard and the cursor will appear in the Phone Number field. Type in the phone line consecutive number (for the first phone line in hunting sequence type in the number 1). Press the TAB key to the Outbound Call field. Click on the Arrow button for the choice and pick one of following: "Y" for making Outbound Calls from this line or "N" for not using the line for Outbound Calls. Repeat steps 2-3 for the rest of the system telephone lines in the hunting sequence. Check the Autoattendant check box to activate this feature. This will enable the Autoattendant button in the Setup window. Click OK to close the window and to return to the main Setup window.

The Outbound Call feature calls customers whose refill orders are ready but were not picked up, or to remind them that their medication is due to be refilled. To use this feature and to create the default schedule of outbound calls, click on the Outbound Calls button to display the Outbound Calls window. Check the Remind check box to activate the feature. To create a schedule for calling out during weekdays click on the Time to call weekdays arrow button. It will bring up a Time window with From field highlighted. First click on the hour the program is to start calling customers. Then click on the minutes past the hour from the Minutes (Min.) row. If minutes are not chosen, double click on the hour. The To field will then be automatically highlighted. Select the time the program is to stop calling and follow the same procedure as above. The Time window will be automatically closed and will return to the Outbound Call window (the scheduled period of time will appear in the Time to Call Weekdays text box). To create a schedule for calling out during weekend click on the Time to Call Sat./Sun. arrow button.

The schedules that the program references when responding to customer requests are created in the form of Templates. Templates allow one to choose the hours that the pharmacy is open on any day, the days it is closed, and to specify how much time to allow preparing an order. Templates are the main building blocks of the working schedule, and are flexible enough to adjust the schedule to any specific situation on a daily basis. The scheduling mechanism allows the program to let customers know when their prescription is going to be ready.

The program manages pickups and/or deliveries, but separate schedules for both of them should be created. In the main Setup window there are two sections—Pickup and Delivery. Check the Pickup check box to activate pickup scheduling and announce to customers the date and time the prescriptions will be ready. Check the Delivery check box if the pharmacy provides delivery service and one wants to activate scheduling of those deliveries.

There are two types of templates: weekly and daily templates. A weekly template consists of the regular business hours during the normal week and covers a full week, including the weekend. Daily templates are additional templates for certain days that have an exceptional schedule, within a normal business week, different from the regular schedule (some holidays and/or days before holidays). The program requires a template for every day of the year except holidays, vacation and days off, if any. Creation of a daily template is similar to the creation of a weekly template except that one need not specify a day of the week and each template covers only one day at a time.

To create Weekly Templates, in the main Setup window check the Pickup check box and/or the Delivery check box, depending on which type of template is to be created. Click on the Templates button in the Pickup or Delivery section. The program will display either the Templates: Pickup or the Templates: Delivery window. Click on the Add button. The Add Template: Pickup or the Add Template: Delivery window will appear. Choose a name for the template and type it in the Template Name text box. Click on Backcolor to choose the background color of the template as it will appear on the calendar. Select a basic color from the Basic colors chart in the Color window and click OK, or refer to Defining Custom Colors to use a color that is not on the basic chart. Choose different colors for the templates, so they can be easily identified on the calendar. Click on the Forecolor button to select the color of the text that appears on the template. Repeat the same process for selecting a background color. Make sure that the Forecolor chosen is different from the background color of the template. In the Template Type section, select the Weekly radial button to create a weekly template. Click on the arrow button in the Day to include in weekly template list box and select from the pull-down list of choices the first day of the week for scheduling. Click on the Add button. The Time window appears with the From field highlighted. Click on the hour the pharmacy opens or the start hour of the delivery period, if creating a Delivery template. Then select the minutes past the hour from the Minutes (Min.) row. If minutes are not needed, double click on the hour. The To field will then be automatically highlighted. Click on the time the pharmacy closes or the last hour of the delivery period, if creating a Delivery template. For example, if the pharmacy opens at 9:00 AM and closes at 8:30 PM, select the 9 from the AM row and the 00 from the Minutes row (or just double click on 9). When the To field is highlighted, select the 8 from the PM row and the 30 from the Minutes row. Multiple working hours during one day may be entered following the procedure described above thus creating "breaks" in the schedule with different preparation or delivery intervals for each one. For example, one may create working hours from 9:00 AM till 1:00 PM with preparation interval one hour and then you may also create another period from 2:00 PM till 8:00 PM with preparation interval two hours for the same day.

To schedule a preparation or delivery interval, highlight the working hours period by clicking on it in the table under the Day to include in weekly template if there is more then one. Then click on the arrow button in the Interval box and choose from the drop-down list of choices a desired preparation or delivery interval to refill or deliver a prescription within highlighted working hours period. Each working hours period may have a different interval assigned to it. The program will use this information to tell customers the time after which their prescriptions will be ready for pickup or delivery. Repeat these steps for every day of the week the pharmacy is open. One may edit any time slot within a given day by selecting it from the table under the "Day to include in weekly template," and either changing the Interval from the drop-down list box or by clicking on the Edit button and reentering the business hours. To erase a working hours interval, highlight it in the table under the "Day to include in weekly template," and click on the Delete button. Click OK when done with the current template. This returns to the Templates screen (either Pickup or Delivery). When finished, click Close.

One may also edit or delete any existing template at any time by selecting it in the Templates list and then clicking on the Edit or Delete button. When one selects template, the description of the template in table forrnat will appear. The process of creating the daily templates is similar to the process of creating the weekly templates. In the main Setup window check the Pickup check box and/or the Delivery check box, depending on which type of template is to be created. Click on the Templates button in the Pickup or Delivery section. The program will display either the Templates: Pickup or the Templates: Delivery window. Click on the Add button. The Add Template: Pickup or the Add Template: Delivery window will appear. Choose a name for the template and type it in the Template Name text box. Later one may create more than one weekly template so select a name that will distinguish between them (e.g., Labor Day, Thanksgiving Day, New Year's Eve, etc.) Click on Backcolor to choose the background color of the template as it will appear on the calendar. Select a basic color from the Basic colors chart in the Color window and click OK, or use a color that is not on the basic chart. Click on the Forecolor button to select the color of the text that appears on the template. Repeat the same process used for selecting a background color. The Forecolor selected should be different from the background color of the template. In the Template Type frame, select the radial button Daily to create a daily template. Click on the Add button. The Time window appears with the From field highlighted. Click on the hour the pharmacy opens or the start hour of the delivery period, if creating a Delivery template. Make sure you are in the correct row for the AM or PM hours. Then select the minutes past the hour from the Minutes (Min.) row. If minutes are not chosen, double click on the hour. The To field will then be automatically highlighted. Click on the time the pharmacy closes or the last hour of the delivery period, if creating a Delivery template. For example, if the pharmacy opens at 9:00 AM and closes at 6:30 PM, select the 9 from the AM row and the 00 from the Minutes row (or just double click on 9). When the To field is highlighted, select the 6 from the PM row and the 30 from the Minutes row. Multiple working hours during working hours from 9:00 AM till 1:00 PM and then create another period from 2:00 PM till 6:30 PM for the same day.

To schedule a preparation or delivery interval, highlight the working hours period by clicking on it in the table under Schedule Setup (if there is more then one period of time in the table). Then click on the arrow button in the Interval box and choose from the drop-down list of choices a desired preparation or delivery interval to refill or deliver a prescription within highlighted working hours period. Each working hours period may have a different interval assigned to it. The program will use this information to tell customers the time after which their prescriptions will be ready for pickup or delivery. One may edit any time slot within a given day by selecting it from the table under "Day to include in weekly template," and either changing the Interval from the drop down list or by clicking on the Edit button and reentering the business hours. To erase a working hours interval, highlight it in the table under "Day to include in weekly template," and click on the Delete button. Click OK when done with the current template. This will return to the Templates screen (either Pickup or Delivery). When finished, click Close. One may also edit or delete any existing template at any time by selecting it in the Templates list and then clicking on the Edit or Delete button. When one selects template, the description of the template in table format will appear underneath.

To define a custom color to be placed in the Custom Colors chart, from the Color screen, click on the Define Custom Colors button. Click on a color area of the color palette. Adjust the illumination and content of the color by moving the white arrow found on the far right of the window down to the desired place. Unless the arrow is moved, the color will remain white. The farther down the arrow is moved, the darker the color. Click the Add to Custom Colors button when you have the desired color. Click on the color just defined from the Custom Colors chart to select it. Click the OK button.

After creating Templates, the next step is Scheduling. Scheduling is the process of applying templates to certain days and weeks of the year. In order to accurately take orders and assign pickup or delivery times, the program will refer to the schedules and preparation times associated with the template for each particular day. Its important to know that the program does not allow for any gaps within any scheduled period of time. Each and every date must have a template assigned to it (even if it's a non-working day) from the first day scheduled in the calendar until the last day chosen to schedule. Schedules for any number of weeks/days up to 3 years in advance may be created. If no template is applied past the current date, the program will automatically extend the current date template one day further.

In the Setup window, click on the Schedule button under either the Pickup or Delivery heading, depending on which type of schedule is to be created. The Schedule: Pickup or Schedule: Delivery window appears. Select the Template to be assigned by clicking on it once in the list of Templates. Use the mouse to move the scroll bar from month to month until the period of the year to be to assigned to the template is presented. If one is assigning a weekly Template, click on any day and the entire week will be highlighted in the color of the template selected in your list of templates. If one is assigning a daily template, then click on the day (or days) to be assigned a template. A daily template can overlap and replace any day(s) already assigned by a weekly template without affecting the schedule of the other days of the week. It is therefore advisable to first apply weekly templates and then overlay daily templates on the dates, which need to be modified. When finished, click OK to save the settings. The schedule for an entire year, should be reviewed to assure that there are no gaps in the schedule.

When a customer calls to order a prescription, the program will ask them to indicate if it is an urgent request. In such a case, a caller will hear: "If this is an emergency call and your prescription must be picked up immediately, press . . . ." Urgent Refills are only offered to customers during business hours. The same templates assigned to the calendar for normal pickups are used to process urgent pickups. However, Urgent Refills have a different (shorter) preparation interval. In the Pickup section of the main Setup window, click on the Urgent Refills button and the Urgent Call Setup: Pickup window will be displayed. Click on the arrow button in the Urgent Prescription Pickup Interval box and from the drop-down list select a preparation interval for Urgent Refills. This interval also determines the period of time before closing that Urgent Refills are offered. If one selects a "0.5 Hour" from the Interval menu, callers will be offered an Urgent Refill option until half an hour before closing. One may choose the option to transfer any urgent call that comes in "late-in-the-day" to the pharmacist. To activate this feature, click the Transfer Late Urgent Calls check box. Enter the number of hours before closing, when any urgent call is considered as "late," in the Hours before closing text box. For example, entering a "1" would transfer any emergency call that is received one hour before closing time to the pharmacist. When finished, click OK to save the settings. An urgent refill order is accepted by the system before transferring the call.

After all the setup procedures are completed, the program is ready to use. The program provided pull down menus or Toolbar buttons on top of the screen to perform different functions.

The Main Screen allows access to all the program's functions and utilities. Getting around the program is easy and intuitive. The upper part of the screen contains the Menus buttons for the tasks one performs as a user. Most of the features are available through both Toolbar buttons and menu commands. The Information Window displays all orders received by the system over the telephone. The Phone Lines Buttons under the Information window show the status of all incoming telephone lines serviced by the system. The Statistics Data Bar at the bottom of Main screen displays the Statistics Data and the current time and date.

The menu bar contains six pull-down menus. The following lists all the options available on the menus:

| Menu Name | Function |
| --- | --- |
| File Menu | |
| Terminal | Starts the Terminal Emulation of the existing pharmacy management system (non-integrated). The RT system must be connected with the pharmacy main PC before starting this feature (optional). |
| Setup | Opens the main Setup window. Deallocates all the telephony lines. |
| Print | Prints all the information displayed on a screen (available if a full-page printer connected to the system). |
| Exit | Exit from the program. |
| Orders | |
| Refill | Displays only refill orders. |
| Doctor | Displays only doctor∝s orders. |
| Message | Displays only voice messages. |
| Unfilled | Display all the orders in the system that have not been marked as filled yet. |
| Current | Displays all the orders that are due for the current day. |
| Show All | Displays all the orders that are currently stored in the system, both filled and unfilled. |
| Phone Log | Displays the phone log containing information about every call processed by the system. |

-continued

| Menu Name | Function |
| --- | --- |
| Search . . . | Enables you to find an order searching by Date, by Type or by RxNumber |
| Actions | |
| Mark As Filled | Marks the selected order as filled. |
| Play Voice Files | Plays Voice Files. Available only if the selected order has a recorded voice file. |
| Data Entry | Displays the Data Entry window for playing and transcribing voice messages and/or adding a note to the selected order. |
| Delete Order | Deletes the selected order from all screens except from the Phone Log screen. |
| Directory | |
| Directory | Displays the Directory window where you can type in Customers and Doctors to be transferred directly to the pharmacy or to the Doctor Menu. |
| Outcall | |
| Pickup Reminder | Displays the Pickup Reminder Outbound Call window where you can type in Customers to be called by the system to remind them that their orders are ready for pickup. |
| Refill Reminder | Displays the Refill Reminder Outbound Call window where you can type in Customers to be called by the system to remind them that their medication is due to be refilled. |

The Toolbar contains buttons, which are graphic representations of utilities or functions that are available from the main screen. One may click on each button to start various commands. Many of the program's features are available both through Toolbar buttons and menu commands. The pop up HELP is available for your convenience by pointing the mouse cursor over a button, which will show a brief description of that button's function.

All information received by the program over the telephone is displayed in the table. As soon as new order comes in, one will hear the sound alert on the computer speakers and a new order will be displayed as the first row in the Information Window. New orders are always highlighted in a light green color. After the new order is processed and the order status is changed to "filled" the order color will be immediately turned to white. One can scroll through the window clicking by the mouse on the appropriate arrows of the scroll bar and select for further processing any order stored in the system. The following is a description of the elements of Information Window.

Row Pointer points to the selected row with black arrow located on the left side of the window. One can move the pointer by clicking on the one wants want to select or by pressing the Up or Down Arrows keys on a keyboard.

Rx Number displays refill numbers in the order they were received with most recent on top of the screen. By clicking on the Rx Number button (on column heading bar) one can sort the orders in ascending order by the Rx numbers. The button will change its color to dark gray.

Call Time displays the date and time the orders have been received in descending order (default). By clicking on the Call Time button one may sort the orders by the incoming date and time in descending order. The button will change its color to dark gray.

Telephone # displays telephone numbers entered by callers where they can be reached. By clicking on the Telephone # button one may sort the orders by the telephone numbers in ascending order. The button will change its color to dark gray. The program will not prompt a caller to enter the phone number where the caller can be reached in case the Rx Number and the phone number detected by the Caller ID match the same data previously entered in any of the Outbound Calls tables. In those cases the caller telephone number will not be displayed in the Telephone # column of the Information Window.

Caller ID displays the callers' telephone numbers captured by the system from the telephone lines. By clicking on the Caller ID button one can sort the orders by the Caller ID numbers in ascending order. The button will change its color to dark gray. By right clicking on a selected row with the Caller ID telephone number the customer name and the phone number will pop-up in a gray frame (available if the phone company can provide the Caller ID service).

Type indicates type of service selected by a caller or how the call has been processed by the system: Pickup indicates that the prescription will be picked up by the customer after due time; Delivery indicates that customer chose the order be delivered; Urgent—indicates that customer will pick up the order in a short period of time; Incompl indicates that customer did not select one of the above or did not listen up to the end of the call processing and hung up. Message indicates that voice mail was left in the system. On the Phone Log screen in addition to all of the above types, may also be shown the following: Rotary indicates calls made from a rotary telephone or by customers just staying on the line. Such calls are automatically transferred to the pharmacy during working hours or to the voice message module after working hours. Hang up indicates calls where a customer did not enter Rx number and hung up. Transfer indicates that the call has been transferred to the pharmacy staff. Verif indicates that a customer called to verify if the order is ready for pickup or delivery. Inform indicates that a customer selected to listen to the General Information about the pharmacy. Pickup Rem/OK indicates that outbound call to a customer for pickup reminding has been made successfully. Pickup Rem/BSY indicates that outbound call to a customer for pickup reminding has been made but at that time the customer's phone line was busy. The system will automatically make four more attempts to call back.

Pickup Rem/NA indicates that outbound call to a customer for pickup reminding has been made but at that time the call was not answered. The system will automatically make four more attempts to call back. Rx Rem/OK indicates that an outbound call to a customer for a refill reminder has successfully been made. Rx Rem/BSY indicates that an outbound call to a customer for a refill reminder has been made but at that time the customer's phone line was busy. The system will automatically make four more attempts to call back.

Rx Rem/NA indicates that outbound call to a customer for refill reminder has been made but at that time the call was not answered. The system will automatically make four more attempts to call back.

Time Due is the date and time when the prescription is going to be ready that has been announced to the customer. Date and time due are determined according to the set of schedules.

Voice indicates whether a voice message has been recorded by a caller for the order represented by the row.

Status shows the information on the current order status. Filled indicates that the order has been processed and ready for pickup or delivery. All orders not marked as Filled are presumed unfilled. Deleted indicates that an order has been deleted by the pharmacy staff.

At the left lower corner of the Main screen there is a row of buttons that show all the incoming telephone lines serviced by the system. Each button controls one incoming telephone line. The consecutive number of the telephone line is shown on each button. When a green light is displayed on the button it means that the line is serviced by the system (allocated) and is free to accept the phone call. If a red light is displayed it means that the line is in service (allocated) and the call is in progress (answered by the system). When no light is displayed on the button (the button is blank) it means that this particular line is reallocated (not serviced by the system at the moment). To Reallocate the telephone line, click on the button representing this line. If the button light is green (the line is free) a dialog box will appear asking for confirmation to reallocate the line. If the button light is red (the line is busy) the system will wait until the phone line becomes free (in order not to interrupt the conversation) and only then a dialog box will appear. Select Yes to reallocate the line, or No to keep the line allocated. If one selects Yes, the message window will appear Wait, while the line is reallocated. Then the line button becomes blank. To Allocate the telephone line, click on the blank button representing this line. A dialog box will appear asking for confirmation to allocate the line. Select Yes to allocate the line, or No to keep the line reallocated. If one selects Yes, the message box will appear asking Wait while the line is allocated. Then a green light will appear on the line button. When the line is allocated the system answers calls after two rings. When the line is reallocated the system does not answer calls and transfers them to the pharmacy after four rings.

Statistics Data Bar are located on the bottom of the Main screen. There are six windows displaying different counters regarding the system activity. From left to right, the following data are displayed: Calls Today, Refills Today, Doctors Today, Messages Today show the total number of calls, refill and doctors orders and messages for the current day respectively. Unfilled shows the total number of unfilled orders in the system. The current time is displayed on the right end of the bar and the current date will immediately pop up if one points the mouse cursor to the current time. As orders are received and filled, the counters will be automatically updated.

To exit the program click the Exit button on the Toolbar, or choose Exit from the File menu or press ALT+F4.

Once orders are received, there are many different ways to display them. Orders are displayed on the Main screen in the Information Window. The program a record of all filled and unfilled orders for up to seven days from the day they were received. Click on the Orders menu. In pull down menu there are a number of options display the orders on the screen. Click one of the menu options or one of the buttons on the Toolbar as follows: Refill to display only refill orders; Doctor to display only doctor's orders; Message to display only voice messages; Unfilled to display all the orders in the system which have not been marked as filled yet; Current to display all the orders which are due for the current day; Show All to display all the orders that are currently stored in the system, both filled and unfilled; Phone Log to display the phone log containing information about every call in the system.

By default all the orders on the screen are displayed in the order they were received (sorted by date and time in descending order). The most recent order is always on top of the screen. To view the orders sorted in a different way one may click on the heading button of the column by which one desires to sort the orders. After sort, the system remembers the sort order and uses it in the fuiture when displaying each of the above screens. The sort order is indicated by the color of column button, which turns to dark gray. One may sort orders by: Rx Number (ascending order); Call Time (descending order); Telephone # (ascending order); Caller ID (ascending order); Time Due (descending order); Status (ascending order). Use the scroll bar to move through the Information Window. One can also use keyboard shortcuts to move through the Information Window, such as the arrow and PgUp/PgDn keys.

The Search menu provides the tools for finding a specific order using a variety of search criteria. Click on the Orders menu. Click on the Search option. On the next pull down menu choose a search method by clicking one of the following: by Date to search based on the date the prescriptions are due; by Type to search based on the type of prescription (Pickup, Delivery, Urgent, Incomplete, Doctor, Message); or by Rx Number to search by the specific Rx number of the prescription. After a search, the search results will be displayed on the Main screen. On the next pull down menu narrow the search by specifying the type of order. Click one of the following: The type of order: Pickup, Delivery, Urgent, Incomplete, and Doctor; Message to search through the voice messages; All to search through all the types of orders.

If searching by Date, the system displays the Date Selection screen. Use the scroll bar to find the month and click the day of that month. Click OK to display all orders that were due on the selected date. If searching by Type, the system displays all refill orders of that type on the Main screen. If searching by Rx Number, the system displays the Rx Number Selection screen. Choose the Rx number from the list by clicking on it and click OK to display the details of the order.

After completing an order, one marks the order as Filled on the Main screen. This changes the order status from Unfilled to Filled. If one is displaying only Unfilled orders, the row will disappear from the Main screen when marked as Filled. Select the order filled by clicking on the row in the Information Window of the Main screen (the row pointer, a black arrow, will point to that row which is highlighted in light green color). Click on the Mark As Filled button on the Toolbar or select the Mark As Filled from the Actions menu. The row will change its color to white and order status will be marked as Filled. If one changes the status of an order from Unfilled to Filled and needs to change it back for some reason, click on the Show Current or Show All buttons on the Toolbar and display the Current or All Orders screens. Select the Marked As Filled order whose status is to be changed back by clicking on the appropriate row. Click on the Clear Status button (which is the same Mark As Filled button crossed now by the red line) on the Toolbar or under the Actions menu select the option Clear Status. The row will change its color back to light green and the order status to unfilled (the status field is blank).

To delete orders, select the order to be deleted by clicking on the row in the Information Window of the Main screen (the row pointer, a black arrow, will point to that row). Click on the Delete Order button on the Toolbar, or select Delete Order from the Actions menu. A dialog box will appear asking for confirmation to delete the order. Select Yes to delete the order, or No to keep the order in the system. If Yes, the order status will be changed to Deleted. The deleted order will be displayed on the screen (in case it is deleted by mistake so that it can be undeleted immediately) until a new order comes or one selects another screen. Then the deleted order will be shown only on the Phone Log screen. All deleted orders are stored in the system and displayed on the Phone Log screen where they can be accessed.

If an order was mistakenly deleted, click on the Phone Log button on the Toolbar. The Phone Log screen will be displayed. Select the deleted order by clicking on it. Click on the Undo Delete button on the Toolbar or select an Undo Delete option from the Actions menu. The order will change its status to Unfilled (the status field is blank) and will appear on all screens highlighted in light green color.

If one has activated the Ask for Refill Message option in the Setup, then any customer who wishes to leave any instructions for the pharmacy staff or include additional items with their order will be offered the option of leaving a voice message specifying their request. The system indicates that a Refill Message has been left if a Yes appears in the Voice column of the Information Window for this refill order. To retrieve the recording of the Refill Message, select an order that includes Refill Message by simply clicking on the row of the Information Window. Click on the Play Voice Files button on the Toolbar or select Play Voice Files option from the Actions menu to hear the recording. If one desired to make a note or transcribe the Refill Message and print it out for reference, click on the Data Entry button on the Toolbar and the Refill screen will be displayed. On the Refill screen one may play voice file by clicking on the Play, Stop, Start, Back, Forward or End buttons; type the information that was recorded in the Memo window; print the typed in information by clicking on the Print button. Choose the printer to print the typed in information by clicking on the Print Setup button (available only if a full-page printer is connected to the system).

If one activated the Doctor's Orders option in the Setup, the system will provide a Main voice menu item "Doctors Only Press . . . " where doctors or their assistants will be prompted to record refill authorizations or a general voice message. Doctor's orders are displayed on the Doctor Orders or All screens with type "Doctor" and blank "Rx Number field. When at least one voice file has been recorded there will be "Yes" in the Voice column. To work with the Doctor's order, select Doctor's order by clicking on the row in the Information Window. One may listen to all the information recorded by the doctor by clicking on the Play Voice Files button on the Toolbar or by selecting Play Voice Files option from the Actions menu. To control the play back of the voice file and/or transcribe the information that was recorded, click on the Data Entry button on the Toolbar. The Doctor screen will be displayed. On the Doctor screen one may; play voice file by clicking on the Play, Stop, Start, Back, Forward or End buttons; type the information that was recorded in the Memo window; print the Doctor Order by clicking on the Print button; choose the printer to print the typed in information by clicking on the Print Setup button (available only if a full-page printer is connected to the system). As Doctors may record prescription information for unlimited number of patients in one recording, one may play and type in the patient's name, address and telephone number and prescription information for each patient individually.

Depending on the setting chosen in the Receipt Printer Setup and the type of printer used, the orders may be printed as follows. With the narrow receipt printer, the system will automatically print every order received. When one clicks on the Print button on the Refill or Doctor screens, the order will be reprinted including the typed information. With a regular full-page printer the system will not automatically print every incoming order. One may print orders in full page format at any time as follows, choose the screen (Unfilled, Refills, Doctors, Phone Log, etc.) to be printed by clicking on the appropriate button on the Toolbar or by selecting from the Orders menu. One may also use the Search option from the Orders menu to print orders sorted by Type or by Date. Under the File menu, click on Print. The Print window appears with a list of the printers that are connected. Select the desired printer by clicking on it (it remains as the printer in use until a different printer is selected). To print the orders displayed on the screen click on the Print button in the Print window. The system prints a full-page document on the printer. For convenience once a printer is selected, one can also use the Print button on the Toolbar at the top of the main screen for all screen printing. A full-page document will be printed on the previously selected printer. In the Receipt Printer modem the printer must be maintained on line otherwise the printing error box will appear on the screen and all the incoming orders will be kept in queue.

If one selected the Activate Voice Messaging option in Setup, then customers may just leave a voice message for the pharmacy staff without placing an order. All voice messages received are stored in the system and can be retrieved through the speakers and/or headphones as follows: select a Voice Message by clicking on the row of the Information Window. Click on the Play Voice Files button on the Toolbar or select Play Voice Files option from the Actions menu to hear the recording. If one would like to make a note or transcribe the Message and print it out for reference, click on the Data Entry button on the Toolbar and the Message screen will be displayed. On the Message screen one may play the voice file by clicking on the Play, Stop, Start, Back, Forward or End buttons. Type the information that was recorded in the Memo window. Print the typed in information by clicking on the Print button. Choose the printer to print the typed information by clicking on the Print Setup button (available only if a full-page printer is connected to the system).

In order to provide more flexible and personalized service to customers and doctors, the program has the Directory of callers who for some reason are not comfortable using the system and who need to be transferred directly to the pharmacy staff entirely bypassing the system. The Directory also the doctors' calls to be routed directly to the Doctor's Voice Menu thus bypassing the Main Voice Menu. Routing the doctors who use the system frequently and who prefer to be immediately routed to the Doctor's Voice Menu will substantially reduce the time of their interaction with the system.

To Add a new customer or doctor to the Directory, click on Directory menu on the Menus bar. The Directory window will appear. Click on the Name text box to place the cursor there. Enter the customer or doctor's name in the Name box. Press TAB on the keyboard or click on the Telephone text box. Enter the customer's or doctor's phone number including the area code in the Telephone text box. The Add button will become enabled. The local area code will always be present in the brackets in the Telephone text box. If the customer's or doctor's phone number has an area code different from the local area code one can easily erase the existing area code and type a new one over it. Press TAB or click on the Note text box. Enter the doctor's office name or comments about the customer in the Note text box. Press TAB or click on the Type drop-down list box. Select Transfer to route all future calls from this customer or doctor directly to pharmacy phones bypassing the system or select Doctor to route all future calls from this doctor directly to the Doctor's Voice Menu. Click on the Add button to enter the new record in the Directory. It will appear as the top line in the window table. Click on the Exit button to close the Directory and save the record. For doctor's offices and customers who have multiple telephone lines which they might use to call to a pharmacy, all phone numbers for those lines have to be entered into the Directory.

To Edit the existing record in the Directory, click on the Directory menu on the Menus bar. The Directory window will appear. Click on the row with the record you want to edit (the row pointer, a black arrow, will point to that row). The information from the selected record will appear in the text boxes for editing. The Edit button will become enabled. One may change the Name, Note and Type of the selected record. Click on the Edit button to change the existing record and all the changes will appear in the selected row. Click on the Exit button to close the Directory. For quickly finding a specific record, sort the records by clicking on the heading button of the column which is to be sorted and display the records. The sort order is indicated by the color of the column button, which turns to dark gray. One may sort records by Name, Office or Telephone in ascending order.

To Add additional telephone numbers for the same caller, click on the Directory menu on the Menus bar. The Directory window will appear. Click on the row with the record to be changed (the row pointer, a black arrow, will point to that row). The information from the selected record will appear in the text boxes. Change the Telephone number of the selected record. The Add button will become enabled. One may also edit the rest of information for this record. Click on the Add button to add an additional telephone number for the same caller. Click on the Exit button to close the Directory.

To Delete the existing record in the Directory, select the record to delete by clicking on the row in the Directory (the row pointer, a black arrow, will point to that row). Click on the Delete button. A dialog box will appear asking for confirmation to delete the record. Select Yes to delete the record, or No to keep the record in the Directory. Select Yes, the record will be deleted. Click on the Exit button to close the Directory.

The Outbound Calls feature allows the system to automatically place reminder calls at certain times to the customers whose refills are ready but have not been picked up or whose prescriptions are due for refill. After the system places the automated call the result of the call appears in the Result column of the Outbound Call directories. OK indicates that outbound call to a customer has been made successfully (the customer answered the call or a message has been left on the customer's answering machine). Pickup, Delivery or Incompl indicate that outbound call to a customer for refill reminding has been made successfully and the customer has immediately ordered the prescription during the outbound call. Calls 1, 2 or 3 indicates that outbound calls to a customer have been made one, two or three times but the customer's phone line was busy or not answered at those times. The system will automatically make up to four attempts to call back. NG indicates that outbound calls to a customer have been made but after four attempts the calls have not gone through.

Refill Reminder calls customers and reminds them that their prescription is due to be refilled. After the outbound calls schedule in the Refill Reminder directory is created, the system automatically calls to the customers at a scheduled time using the designated phone lines and informs them that a certain prescription (Rx Number) is due for refill. The customer has an option to place a refill order immediately during the outbound call, scheduling a pickup or a delivery.

To Add a new customer or a new Rx Number to the Refill Reminder directory, select Refill Reminder from the OutCall menu. The Refill Reminder Outbound Call window appears. Enter the customer's name in the Name text box. Press TAB on the keyboard or click on the Telephone text box. Type the customer's phone number including the area code in this field. The local area code will always be present in the brackets in the Telephone text box. It can be changed by erasing the existing local area code and entering a phone number with a different area code. Press TAB or click on the Rx Number text box. Enter the Rx Number of the prescription, which is due to be refilled. The Add button will become enabled. Click on the Add button to enter the new record in the Refill Reminder directory. By default it will appear in the directory in the sorted by name row to be called at the scheduled date and time (as it has been previously scheduled in the Setup). Click on the Exit button to close the Refill Reminder directory. Every Rx Number for each customer has to be entered as a separate record. To enter a duplicate record, a dialog box will appear asking for confirmation to update the duplicated record. Select Yes to update the record, or No to keep the record in the Directory. If Yes, the outbound call will be scheduled at the default date and time (as it has been previously scheduled in the Setup).

To Edit the existing record in the Refill Reminder directory, select Refill Reminder from the OutCall menu. The Refill Reminder Outbound Call window appears. Click on the row with the record for edit (the row pointer, a black arrow, will point to that row). The information from the selected record will appear in the text boxes for editing. The Add and Edit buttons will become enabled. For quickly finding the specific record, sort the records by clicking on the heading button of the column for sort and display the records. The sort order is indicated by the color of the column button, which turns to dark gray. One may sort records by Rx Number, Telephone or Name in ascending order. One may make changes in the Rx Number, Telephone or Name text boxes for the selected record. Click on the Edit button to change the existing record and all the changes will appear in the selected row to be called at the default date and time. Click on the Add button to add an additional record for the same customer. By default it will appear in the directory in the sorted by name row to be called at the scheduled date and time. Click on the Call field of the selected row to change the call status and the arrow button will appear. Click on the Arrow button and a drop-down list box will appear. Select "Y" for making an outbound call at the default date and time. Select "N" to cancel a call for this record (can be change to "Y" at a later time). Click on the Date field to edit the date of calling out Date window will be displayed. Use the scroll bar to find the month and click on the desired day of that month. Click OK and the selected date will appear in the Date field of the selected row. Click the time field of the selected row to edit a scheduled time for calling out. It will bring up a Time window with the From field highlighted. First click on the hour the program is to start calling out to customers. Then click on the minutes past the hour from the Minutes (Min.) row. If minutes are not chosen, double click on the hour. The To field will be automatically highlighted. Select the time the program is to stop calling out. The Time window will be automatically closed and the scheduled period of time will appear in the selected Time field. Click on the Exit button to close the Refill Reminder directory.

To Delete the existing record in the Directory, select the record to be deleted by clicking on the row in the Refill Reminder directory (the row pointer, a black arrow, will point to that row). Click on the Delete button. A dialog box will appear asking for confirmation to delete the record. Select Yes to delete the record, or No to keep the record. If Yes, the record will be deleted. Click on the Exit button to close the Refill Reminder directory.

One may make automated calls to customers whose refills are ready but have not been picked up. The process of using the Pickup Reminder Outbound the same as Refill Reminder Outbound Calls.

To Add a new customer or a new Rx Number to the Pickup Reminder directory, select Pickup Reminder from the Out-Call menu. The Pickup Reminder Outbound Call window appears. Follow the steps for adding a New Record, above.

To Edit the existing record in the Pickup Reminder directory, select Pickup Reminder from the OutCall menu. The Pickup Reminder Outbound Call window appears. Follow steps for editing the record, above.

To Delete the existing record in the Directory, select the record to be deleted by clicking on the row in the Pickup Reminder directory (the row pointer, a black arrow, will point to that row). Follow the steps for Deleting the Record, above.

The remote prescription refill system of the present invention differs from the stand-alone system in that a number of functions are allocated to a remote location. In the remote system of the present invention, the call answering feature of the invention can be transferred to a central station. Appropriate computer equipment and associated software is in place at the central station to permit refill order information to be obtained at the central station. This refill order information can then be forwarded to the pharmacy in any of a number of ways.

As shown in the flowchart of FIG. 1, a caller calling the pharmacy can be dealt with in one of four different ways depending on how the user pre-sets the functions of the system.

In Case 1, the Pharmacy main phone line is call forwarded to the central station telephone number when the pharmacy is closed. In Case 2, the Pharmacy main phone line is call forwarded to the central station telephone number temporarily during peak periods. In Case 3, if all pharmacy lines are busy overflow calls are forwarded to the central station telephone number. In Case 4, the Pharmacy has designated the central station telephone number as the refill phone line seven days a week, twenty-four hours a day.

The central station automatically processes, receives, schedules and transmits the refill pharmacy orders. The central station can refill order information in any of a number of ways. For example, all after-hours orders can be transmitted in a batch, when the pharmacy opens, or the central station can transmit orders at specified intervals during pharmacy working hours, or the central station can transmit orders when the pharmacist calls to retrieve the orders.

Orders can be sent by the central station to the pharmacy in one or more of a number of ways such as via telefax, or via modem to a pharmacy PC programmed to receive the orders over the Internet or via e-mail, or on a pharmacy pager, or in some combination. If a PC is used by the pharmacy, a portion of the stand-alone software is utilized to permit the pharmacist to view the orders and to hear voice messages.

The present invention also differs from the stand-alone system in that there is no need for hardware or software resident in the individual pharmacy receiving telephone calls. Rather, calls coming to all or selected telephone lines in the pharmacy can be forwarded via a toll-free number to the central station's central server, where orders for prescription refills can be input via the customer's touch tone telephone buttons and/or voice messages can be recorded. These orders are then forwarded to the pharmacy in one of the desired manners.

To the customer or doctor whose call is answered by the remote refill systems of the present invention, it appears as if a computer in the pharmacy is answering the call. He/she can key in one or more Rx numbers and/or leave a voice message with special instructions such as additional items to be included in the order. The pharmacist has an option to record sale promotion announcements and change them at any time. The present invention can also provide multilanguage support to pharmacy customers.

In the remote system invention, most of the setup functions and options described in connection with the stand-alone system are now resident in central server rather then in a computer resident in the pharmacy, and are performed, where necessary, by central station personnel rather than the pharmacy staff.

The detailed operations of the remote refill system of the present invention for the customer, the pharmacy subscriber and the central station staff are hereinafter described.

When a pharmacy implements service under the present invention, the pharmacy receives a specific telephone number, preferably a toll-free number to a central station to which a pharmacy calls will be forwarded. Additionally, the pharmacy will obtain a password for orders retrieval. The system is then available to be used by the pharmacy in a number of different ways, at the option of the pharmacy staff:

After-hours Service: To take refill orders and/or voice messages when the pharmacy is closed, the pharmacy must order the Call Forwarding feature from the local telephone company for the main pharmacy telephone line and activate it when the pharmacy is closed.

Overflow Service: To answer "overflow" calls—that is, when during working hours all pharmacy telephone lines are busy or not being answered, the system of the present invention can be used to answer the calls and either take a refill order and/or allow the customer or doctor to leave a voice message. For this service the pharmacy must order "Call Forwarding-Busy Line/Don't Answer" from the local telephone company, and when all lines are in use or are not being answered, all incoming calls will be automatically forwarded to a pre-set toll-free telephone number at the central station.

Peak Time Service: To answer all telephone calls to a pharmacy and take refill orders and/or ask the customer or doctor to leave a voice message (used mostly when the staff is too busy to answer the telephone during peak periods of store activity), regular Call Forwarding is needed for the main telephone line and can be activated when needed.

Dedicated Refill Line Service: To answer all calls to a separate toll free telephone line advertised by the pharmacy as the special "refill line" to call when the customer wishes to only order a prescription refill (with an optional voice message attached to the order), the pharmacy needs to advertise, as a special refill line, the toll free number provided by the central station.

During sign up for the invention, the pharmacist should provide the following data to be entered into the setup of the pharmacy account in the central server: the pharmacy name, approved texts of initial greeting, general information and after-hours announcements to be professionally recorded and uploaded into the central server; the pharmacy's local area code and voice phone numbers; the work schedule for a regular week and for all holidays when the pharmacy is open (FIG. 6.); all holidays and other specific days when the pharmacy is closed (FIG. 5); length of refill identification number; length of customer phone number (with or without area code); prescription preparation interval for scheduling refill pickup or delivery; select foreign languages if multilingual support is desired; the pharmacy FAX number and/or the modem telephone line number and/or pharmacy pager number and/or e-mail address for order transmission.

When the central service setup is complete by the central station staff and the service is activated, the server is ready to receive the call in orders and messages at any time, 24 hours a day. At specified intervals, this central server automatically calls the pharmacy and transmits all the orders to the pharmacy that have arrived since the last time orders were transmitted such transmission can take place in one of five ways:

1. To a fax machine. 2. To a personal computer at the pharmacy by modem. The pharmacy, utilizing a portion of the software from the stand-alone version can handle and utilize the information in much the same way as the stand-alone system, despite the fact that the refill orders re being placed at a remote location. Thus, all orders appear on a monitor (through modem dial-up connection or over the Internet). 3. To a pharmacy numeric and alpha-numeric pager (which can also be used as a alternative way of communication in emergency cases and when pharmacy FAX or modem does not respond). 4. To a pharmacy e-mail address (if any). Alternatively, the refill order information can remain at the central station and be retrieved by the pharmacy by calling in to the central station.

Where a voice message is attached to the order, it is so indicated in the order transmitted to the pharmacy report and the pharmacy staff can call the central station at the same toll free number to retrieve the messages and/or orders as they are saved in the central computer. With the client software installed in the pharmacy PC, voice messages can be retrieved through the PC speakers by pointing and clicking on the order. Client software installed in the pharmacy PC is a short but a fall multimedia version of the stand-alone version of the software and includes modem and e-mail communication modules.

The central station, service center, is a centralized facility where a single computer could be located or specialized servers could communicate over a LAN. Each server or group of servers performs specific finctions and exchanges information with other servers. In a preferred embodiment, the invention consists of the following servers: Database Server (DS)—dedicated Windows NT server running Microsoft SQL Server DBMS. DS hosts the database Refill that stores all the data on the system. A number of SQL Server stored procedures are used to retrieve and manage data. There are the following tables in Refill database: Lines—the table contains configuration and description of all the servers on the system. It is used to reconfigure servers by allocating or deallocating lines. Refill—main table that stores all the orders and other call information. CommPorts—table that sets the configuration of communication ports on all the servers. There are a few other auxiliary programs that reside on Database server: Setup with MS Access Setup Database (SD). SD resides on DS but can be accessed and modified from any computer on the network that has a client copy of Setup program and proper access authority. SQLMonitor—program that constantly monitors the status of all the servers on the network and produces the pager alert if any of the servers do not respond properly. Telephony/Fax Server (TFS)—computer that takes telephone refill orders, doctors' scripts and voice messages for the pharmacy staff and sends the fax with Transaction Log to the store. Multiple TFSs are connected to DS via the LAN. TFS is the Windows NT client with multiple Dialogic telephony and fax boards installed. Up to three T1 telephone lines will terminate at each TFS. TFSs can only communicate and exchange data with DS.

The following programs are running on the TFS: T1VoiceFaxManager—server program that monitors and supervises up to 72 telephone lines (T1 time slots) for accepting the incoming and outgoing telephone and fax calls. T1VoiceFax—client program that handles one specific telephone line (T1 time slot) and actually processes incoming and outgoing voice and fax calls. Up to 72 T1VoiceFax programs can run on each TFS. Modem Server (MS)—computer that transmits transactions (including digitized voice files) taken by TFS to workstation in the pharmacy. Transactions can then be accessed through client GUI screens. Multiple MSs are connected to DS via the LAN. MS is the Windows NT client with multiple analog or digital modems installed. MSs can only communicate and exchange data with DS. The following programs are running on the TFS: T1ModemManager—server program that monitors and supervises all modem connections. T1Modem—client programs that actually transmit data through individual communication port. Internet Server (IS)—computer that hosts RT Web site. Pharmacy customers can log on to the Web site from anywhere in the world and order their prescription refills. Orders, entered through the Internet are inserted into the Refill database on DS and the pharmacy can be notified either via fax (VFS) or modem (MS).

The Initial Announcement is the first announcement customers hear when they access the invention. At least one initial announcement should always be present. The General Announcement is a feature that may provide callers with general information about the pharmacy (e.g., hours, directions, promotional and sale information etc.) The After-Hours Announcements will only be played when the store is closed and provides callers with after-hours emergency related information.

The present invention requests customers' phone numbers in case they need to be reached. The "Seven Digits" customer phone number in the sign up sheet is chosen if the pharmacy services a local region with only one area code and one does not want to request an area code with the customer's phone number. The "Ten Digits" customer phone number in the sign up sheet is chosen if the pharmacy serves customers from more than one area code region The invention requires that the number of digits in the Rx Number used in the Pharmacy (any number between 3 and 10 excluding letters, preceding or succeeding if any) be specified. The invention will validate a customer's entry to ensure the correct number of digits has been punched in. If necessary (for example, if one uses Rx numbers of two different lengths) one may choose a variable length for the Rx number. If the variable length of the Rx number is chosen, the system will prompt customers to follow the input of the Rx number by the "#" sign. In any case, the system will play back to customers the entered Rx numbers for verification.

To start the resident version of the invention, i.e., where there is a PC at the pharmacy utilizing the "front-end" of the software, turn the power on to start the computer. On the Windows desktop screen click on the Start button. Click on Programs and then click on the invention's icon. When the program starts, it displays the title screen briefly and then the main screen appears, It is important to check that the computer's date and time settings are correct before starting the invention.

To access the Setup screen, click on File-Setup and the Setup screen will be displayed. When you finished, click OK to save the settings .

Figure 2:
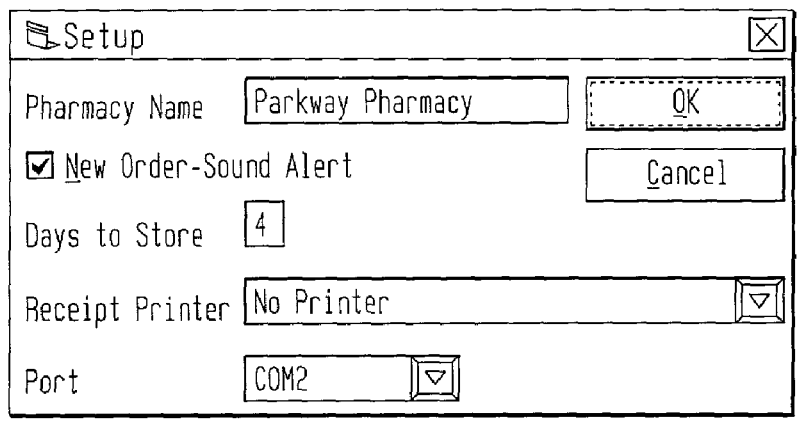
FIG. 2 is a computer display of a setup function of the invention.

Pharmacy Name (FIG. 2)—When first starting the invention, enter the pharmacy name in the Setup window by typing the name of the pharmacy into the Pharmacy Name text box.

New Order Sound Alert (FIG. 2)—When a new order is received, its arrival may be immediately announced by a sound from computer speakers. Check the New Order—Sound Alert check box to activate this feature.

Storing Orders (FIG. 5)—The choose the number of days' worth of orders (from 2 to 7 days) that will be stored in the system and displayed on the main screen may be chosen. Click on the Days to Store text box and delete the existing number. Type in the desired number of days for storing orders in the system.

Printing (FIG. 4)—There are two different ways of printing orders in the invention, Receipt Printing and Full-page Printing.

Receipt Printing—All orders are printed automatically on the receipt (cash register type) printer in the form of order slip as soon as they are received. Click on the arrow in the Receipt Printer list box and select the desired receipt printer from the drop-down choices to enable this feature. If printing is not needed, choose option "No Printer."

Full-Page Printing—The invention can print in the full-page format on any printer connected to the computer and installed in the Windows system. In full-page printing mode orders sorted on the Main Screen can be printed in a variety of way (refills, filled, doctor's orders, messages, etc.) in full-page format.

Figure 3:
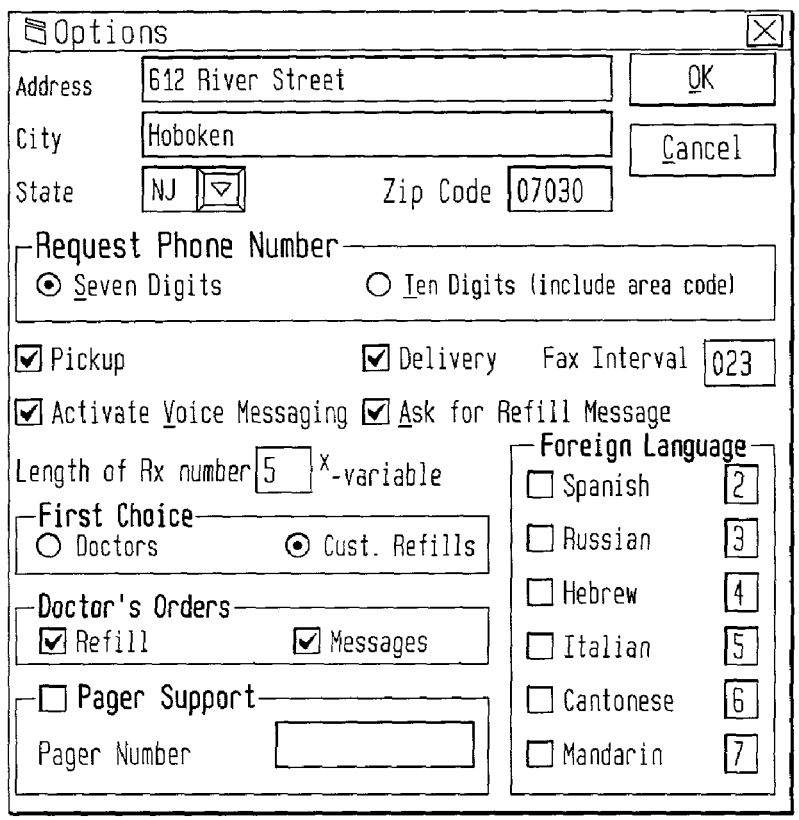
FIG. 3 is a computer display of some available options of the invention.
Figures 4, 5:
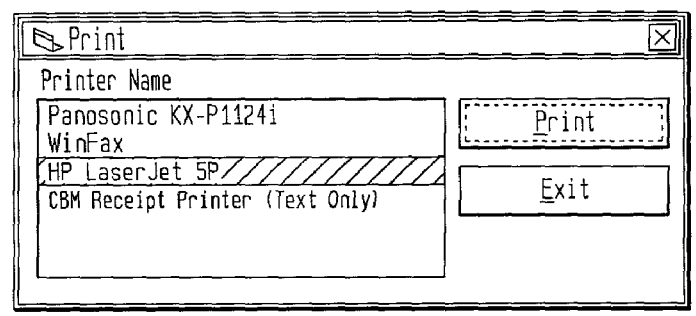
FIG. 4 is a computer display of some available announcement options of the invention.
FIG. 5 is a computer display of some available print options of the invention.

FIG. 3 is the Options screen wherein the address of pharmacy is input, the amount of the phone number digits can be requested (seven or ten), and other options can be set. FIG. 4 is the announcement screen where announcements can be selected. FIG. 5 is the holiday schedule screen where holidays can be selected. FIG. 7 is the pharmacy schedule screen where the pharmacy schedule can be set.

After the setup procedures, are complete, the invention operates using either pull down menus or the Toolbar buttons on top of the screen to perform different functions.

The Main Screen allows access all the functions and utilities. The upper part of the screen contains the Menus and the Toolbar buttons for the tasks. Most of the features are available through both Toolbar buttons and menu commands. The Information Window displays all orders received by the system over the telephone. The Statistics Data Bar at the bottom of Main screen displays the Statistics Data.

The menu bar contains four pull-down menus. The following table lists all the options available on the menus.

| Menu Name | Function |
| --- | --- |
| File Menu | |
| Setup | Opens the main Setup window. Deallocates all the telephony lines. |
| Print | Prints all the information displayed on a screen (available if a full-page printer connected to the system). |
| Exit | Exit from the program. |
| Orders | |
| Doctor | Displays only doctor∝s orders. |
| Message | Displays only voice messages. |
| Unfilled | Display all the orders in the system that have not been marked as filled yet. |
| Current | Displays all the orders that are due for the current day. |
| Show All | Displays all the orders that are currently stored in the system, both filled and unfilled. |
| Phone Log | Displays the phone log containing information about every order received by the system. |
| Actions | |
| Mark As Filled | Marks the selected order as filled. |
| Play Voice Files | Plays Voice Files. Available only if the selected order has a recorded voice file. |
| Data Entry | Displays the Data Entry window for playing and transcribing voice messages and/or adding a note to the selected order. |
| Delete Order | Deletes the selected order from all screens except from the Phone Log screen. |

The Toolbar contains buttons, which are graphic representation of utilities or functions of the invention that are available from the main screen. Each button starts various commands. The pop up help is available by pointing the mouse cursor over a button, which will show a brief description of that button's function.

All information received by the invention over the telephone is displayed in the table. As soon as a new order comes in, a sound alert on the computer speakers is generated and a new order(s) will be displayed as the first row(s) in the Information Window. New orders are always highlighted by color. After processing the new order and changing the order status to "filled" the order color is immediately changed.

Row Pointer points to the selected row with a black arrow located on the left side of the window. Move the pointer by clicking on the row to be selected or by pressing the Up or Down Arrows keys on a keyboard.

Figure 9:
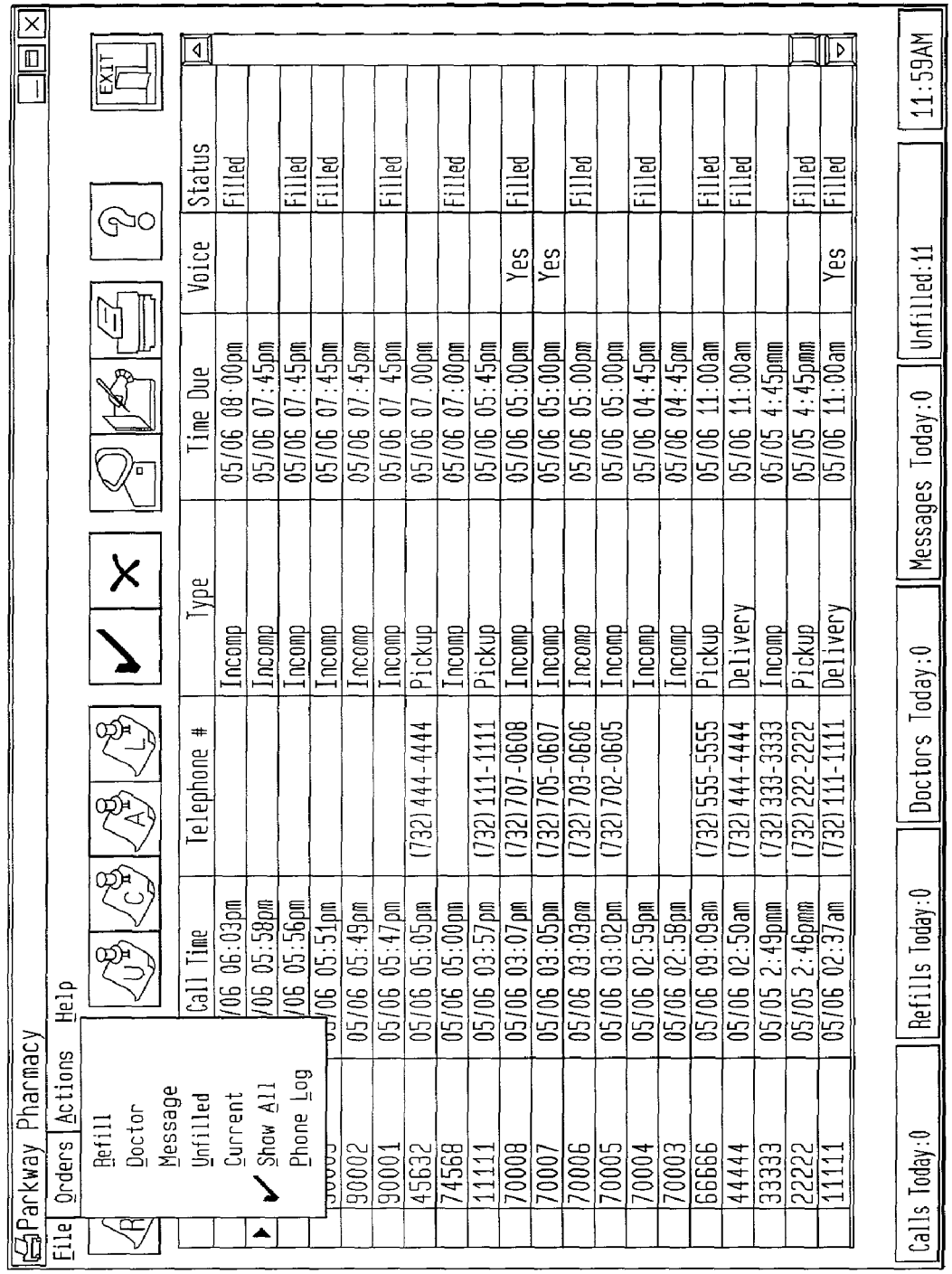
FIG. 9 is a computer display of refill orders or FIG. 8, with sort options for these orders.

Rx Number (FIGS. 8-9) displays refill numbers in the order received with most recent on top of the screen. Clicking on the Rx Number button (on column heading bar), sorts the orders in ascending order by the Rx numbers. The button changes its color.

Call Time (FIGS. 8-9) displays the date and time the orders have been received in descending order (default). Clicking on the Call Time button sorts the orders by the incoming date and time in descending order. The button will change its color.

Telephone # (FIGS. 8-9) displays telephone numbers entered by callers where they can be reached. Clicking on the Telephone # button sorts the orders by the telephone numbers in ascending order. The button will change its color.

Type (FIGS. 8-9) indicates type of service selected by a caller or how the call has been processed by the system; Pickup indicates that the prescription will be picked up by the customer after due time; Delivery indicates that customer chose that the order be delivered; Incompl indicates that customer did not select one of the above or did not listen up to the end of the call processing and hung up.

Doctor indicates Doctor's call.

Message indicates that voice mail was left in the system.

On the Phone Log screen in addition to all of the above types, may also be shown the following: Rotary indicates calls made from a rotary telephone or by customers just staying on the line. Such calls are automatically routed to the voice message module. Hang up indicates calls where a customer did not enter Rx number and hung up. "Inform" indicates that a customer selected to listen to the General Information about the pharmacy.

Time Due (FIGS. 8-9) shows date and time when the prescription is going to be ready that has been announced to the customer. Date and time due are determined according to the set of schedules programmed in the invention.

Voice (FIGS. 8-9) indicates if a voice message has been recorded by a caller for the order represented by the row.

Status (FIGS. 8-9) shows the information on the current order status. Filled indicates that the order has been processed and ready for pickup or delivery. All orders that are not marked as Filled are presumed unfilled. Deleted indicates that an order has been deleted by the pharmacy staff.

Statistics Data Bar (FIGS. 8-9) On the bottom of the Main screen there are six windows displaying different counters regarding the system activity. From left to right, the following data are displayed: Calls Today, Refills Today, Doctors Today, Messages Today show the total number of calls, refill and doctors orders and messages for the current day respectively. Unfilled shows the total number of unfilled orders in the system. As orders are received and filled, the counters will be automatically updated.

Orders may be sorted and viewed in different ways. Orders are displayed on the Main screen in the Information Window. The invention keeps a record of all filled and unfilled orders for up to seven days from the day they were received.

Click one of the following menu options or one of the following buttons on the Toolbar (FIG. 9): Refill to display only refill orders; Doctor to display only doctor's orders; Message to display only voice messages; Unfilled to display all the orders in the system which have not yet been marked as filled; Current to display all the orders which are due for the current day; Show All to display all the orders that are currently stored in the system, both filled and unfilled; and Phone Log to display the log containing information about every order in the system including deleted ones.

By default all the orders on the screen are displayed in the order received (sorted by date and time in descending order). The most recent order is always on top of the screen. To view the orders sorted in a different way, click on the heading button of the column by which the orders are to be sorted. After the sort, the invention remembers the sort order chosen and uses it in future when displaying each of the above screens. The sort order is indicated by the color of column button. Orders can be sorted by: Rx Number (ascending order); Call Time (descending order); Telephone # (ascending order); Time Due (descending order); Status (ascending order).

After completing an order, it is marked as Filled on the Main screen. This changes the order status from Unfilled to Filled. If displaying only Unfilled orders, the row will disappear from the Main screen when marked as Filled. Select the order filled by clicking on the row in the Information Window of the Main screen (the row pointer, a black arrow, will point to that row which is highlighted in color). Click on the Mark As Filled button on the Toolbar or select the Mark As Filled from the Actions menu. The row will change its color and order status will be marked as Filled. If the status of an order from Unfilled to Filled must be changed back, click on the Show Current or Show All buttons on the Toolbar and display the Current or All Orders screens. Select the Marked As Filled order whose status is to be changed back by clicking on the appropriate row. Click on the Clear Status button (which is the same Mark As Filled button crossed now by a red line) on the Toolbar or under the Actions menu select the option Clear Status. The row changes its color back to its original color and the order status to unfilled (the status field is blank).

To delete an order, select the order to be deleted by clicking on the row in the Information Window of the Main screen (the row pointer, a black arrow, will point to that row). Click on the Delete Order button on the Toolbar, or select Delete Order from the Actions menu. A dialog box will appear asking confirmation to delete the order. Select Yes to delete the order, or No to keep the order in the system. If Yes, the order status will be changed to Deleted. The deleted order will be displayed on the screen (in case it was deleted by mistake and would like to undelete it immediately) until a new order comes or another screen is selected. Then the deleted order will be shown only on the Phone Log screen. All deleted orders are stored in the system and displayed on the Phone Log screen where they can be accessed. If an order was deleted by mistake and would like to reverse this action, click on the Phone Log button on the Toolbar. The Phone Log screen will be displayed. Select the deleted order by clicking on it (for quickly finding the deleted order sort orders by status by clicking on the column Status button). Click on the Undo Delete button on the Toolbar or select an Undo Delete option from the Actions menu. The order will change its status to Unfilled (the status field is blank) and will appear on all screens highlighted in a color.

Any customer who wishes to leave any instructions for the pharmacy staff or include additional items with their order will be offered the option of leaving a voice message specifying their request. The invention indicates that a Refill Message has been left if a Yes appears in the Voice column of the Information Window for this refill order. To retrieve the recording of the Refill Message, select an order that includes Refill Message by clicking on the row of the Information Window. Click on the Play Voice Files button on the Toolbar or select Play Voice Files option from the Actions menu to hear the recording. To make a note or transcribe the Refill Message and print it out for reference, click on the Data Entry button on the Toolbar and the Refill window will be displayed.

On the Refill window one may play the voice file by clicking on the Play, Stop, Start, Back, Forward or End buttons; type the information that was recorded in the text window; or print the order with the typed in information by clicking on the Print button. Choose the printer to print the order with the typed in information by clicking on the Print Setup button (available only if a full-page printer is connected to the system).

Doctor's Orders provides a Main voice menu item "Doctor Office Only Press . . . " where doctors or their assistants will be prompted to record new prescriptions or refill authorizations or a general voice message. Doctor's orders are displayed on the Doctor Orders or All screens with type "Doctor" and blank "Rx Number" field. When at least one voice file has been recorded there will be "Yes" in the Voice column. To work with the Doctor's order, select Doctor's order by clicking on the row in the Information Window.

Figure 10:
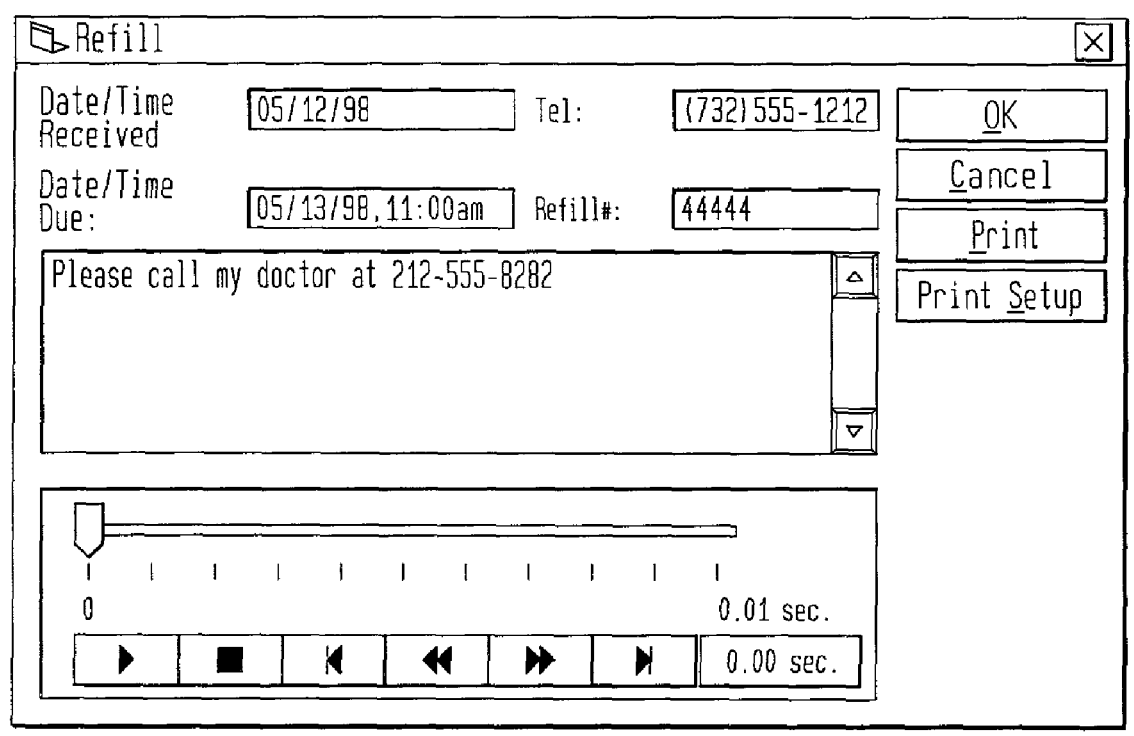
FIG. 10 is a computer display of voice messages which may be printed or played.

One may listen to all the information recorded by the doctor by clicking on the Play Voice Files button on the Toolbar (FIG. 10) or by selecting Play Voice Files option from the Actions menu. To control the play back of the voice file and/or transcribe the information that was recorded, click on the Data Entry button on the Toolbar. The Doctor window will be displayed. On the Doctor window one may; play voice file by clicking on the Play, Stop, Start, Back, Forward or End buttons; type the information that was recorded in the text window; or print the Doctor Order by clicking on the Print button. Choose the printer to print the Doctor Order with the typed in information by clicking on the Print Setup button (available only if a full-page printer is connected to the system).

Doctors may record prescription information for unlimited number of patients in one recording. You may play and type in the patient's name, address and telephone number and prescription information for each patient individually.

With a narrow receipt printer, the system automatically prints every order received. Click on the Print button on the Refill (FIG. 5) or Doctor windows so that the order will be reprinted including the typed information. With a full-page printer, the system will not automatically print every incoming order. Print orders in full page format at any time by choosing the screen (Unfilled, Refills, Doctors, Phone Log, etc.) by clicking on the appropriate button on the Toolbar or by selecting from the Orders menu. Under the File menu, click on Print. The Print window appears with a list of the printers that are connected to the computer. On the Print window select the desired printer by clicking on it. then click on the Print button. A full-page document will be printed on the selected printer. Once a printer is selected, use the Print button on the Toolbar at the top of the main screen for all full-page printing. A full-page document will be printed on the previously selected printer. The Print button is disabled when a receipt printer is also installed in the system. In the Receipt Printer mode, the printer must be kept on line otherwise the printing error box will appear on the screen and all the incoming orders will be kept in queue until the error is corrected.

Activate Voice Messaging permits customers to leave a voice message for the pharmacy staff without placing an order. All voice messages received are transmitted to the computer and can be retrieved through the speakers and/or headphones as follows: select a Voice Message by simply clicking on the row in the Information Window; click on the Play Voice Files button on the Toolbar or select Play Voice Files option from the Actions menu to hear the recording. To make a note or transcribe the Message and print it out for reference, click on the Data Entry button on the Toolbar and the Message window will be displayed. On the Message window one may: play the voice file by clicking on the Play, Stop, Start, Back, Forward or End buttons; type the information that was recorded in the text window; or print the typed in information by clicking on the Print button. Choose the printer to print the typed information by clicking on the Print Setup button and selecting the desired printer on the Print Setup window (available only if a full-page printer is connected to the system).

Figure 11:
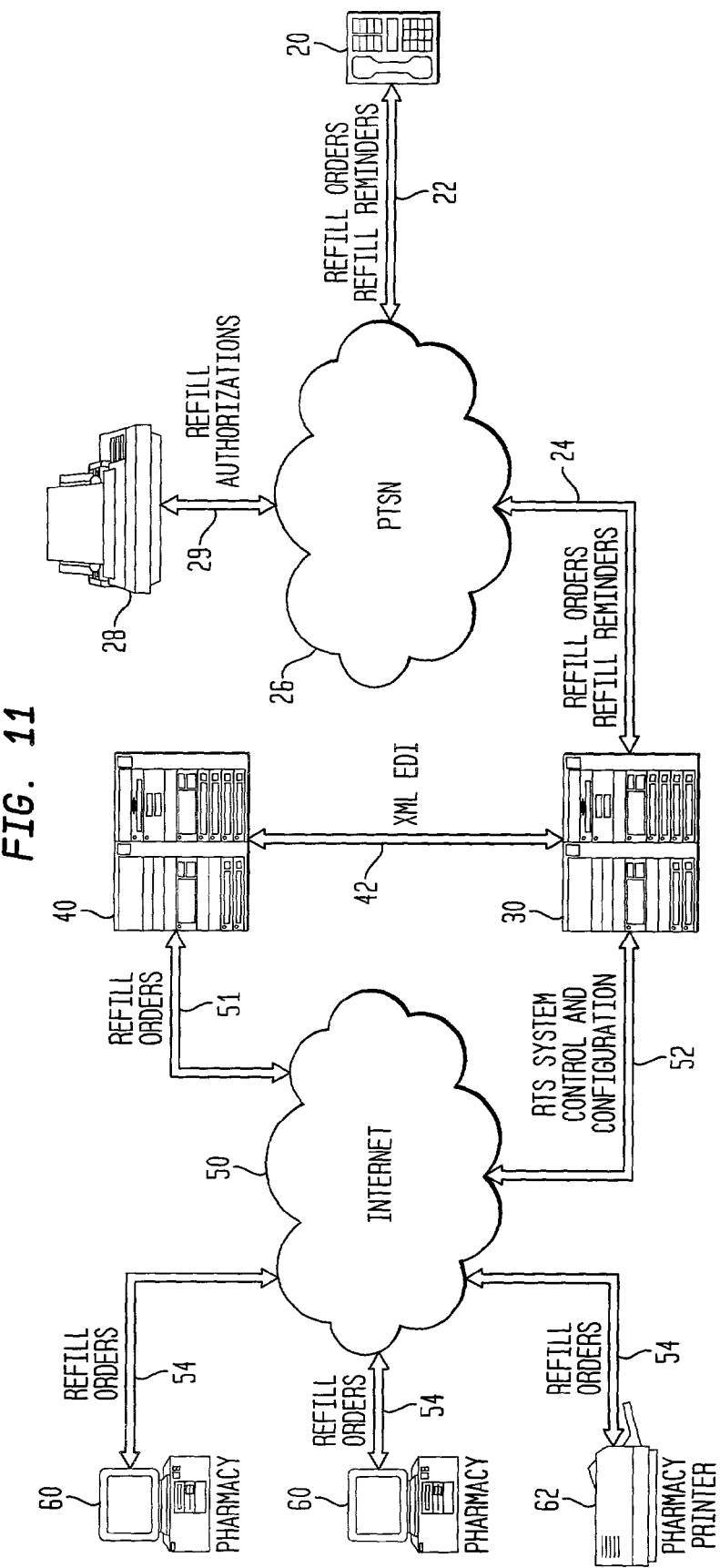
FIG. 11 is a schematic diagram of another embodiment of the present invention wherein the central station can communicate with a pharmacy management system to electronically confirm prescription refill availability.

FIG. 11 is a schematic diagram of another embodiment of the present invention wherein the central station can communicate with a pharmacy management system to electronically confirm prescription refill availability. As can be seen, a customer can use a customer telephone 20 to connect to the central station 30 over a public telephone service network (PTSN) 26 through connection paths 22 and 24. The customer can call in refill orders, and the central station 30 can send refill reminders. Doctors can send refill authorizations over the PTSN 30, typically by facsimile from office fax machines 28 over connection path 29 to the central station 30. The central station 30, responsive to a refill request from a customer, can communicate with a pharmacy management system 40 over electronic data interface 42, which would typically be in XML, to verify that such refill request is authorized. If so, the central station 30 could continue to process the refill request. Additionally, the central station 30 could advise the customer as to any relevant information received from the pharmacy management system 40. If not, the central station 30 could contact the doctor via facsimile to request refill authorization.

If the refill request is authorized by the pharmacy management system 30, the central station 30 completes order with the customer over the telephone and sends the completed order (including an optional voice message) to the pharmacy management system 40, over the connection 42 or over the Internet, which in turn delivers the refill order information to the pharmacies 60 over the Internet 50 via connections 51 and 54. Pharmacies 60 can also perform central station control and configuration tasks such as exhibited in FIG. 14 over the Internet via connections 52. In another embodiment, the pharmacy management service is not central but located at the pharmacy, and the central station 30 communicates order information thereto over the Internet via connections 52 and 54.

Figure 12:
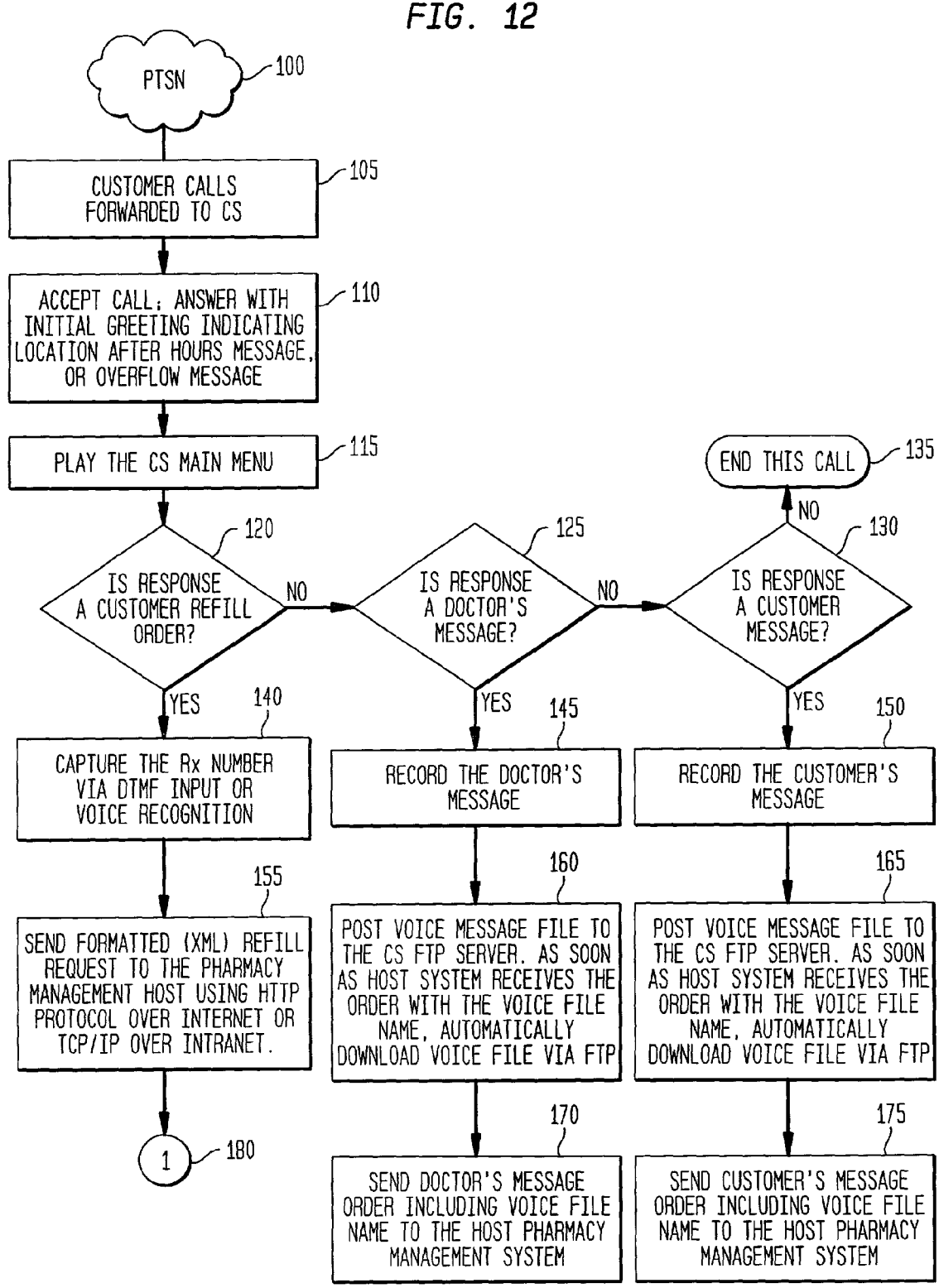
FIG. 12 is a flow chart of the process of the invention shown in FIG. 11.

Referring now to FIG. 12, a flow chart of the operation of this embodiment of the invention is provided. A call coming over a public telephone service network 100 is directed to a pharmacy. If desired, the pharmacy can have a customer call forwarded to the central station at 105. The call is accepted at the central station at 110 and answered with initial greeting indicating location, after hours message or overflow message. At 115, the central station provides a main menu. If the customer indicates that the call is for a customer refill at 120, the prescription number is captured via DTMF input or voice recognition at 140 and is formatted to XML language and a request is sent to the pharmacy management host at 155 using HTTP protocol over the Internet or TCP/IP protocol over the Intranet. If the customer is not calling for a refill at 120, the call may be a doctor's message at 125. If so, the doctor's message is recorded at 145, and the voice message file is posted to the central station FTP server at 160. As soon as host system receives the order with the voice file name, the voice file is automatically downloaded via FTP. At 170 the doctor's message order is sent, including the voice file, to the pharmacy management system. If the response to the main menu 115 is a customer message at 130, the customer's message is recorded at 150 and at 165 the voice message file is posted to the central station FTP server. As soon as the host system receives the order with the voice file name, the voice file is automatically downloaded via FTP. At 175 the customer's message is sent including a voice file name to the pharmacy management system. If the answers to the menu 115 are none, the call is ended at 135.

Figure 13:
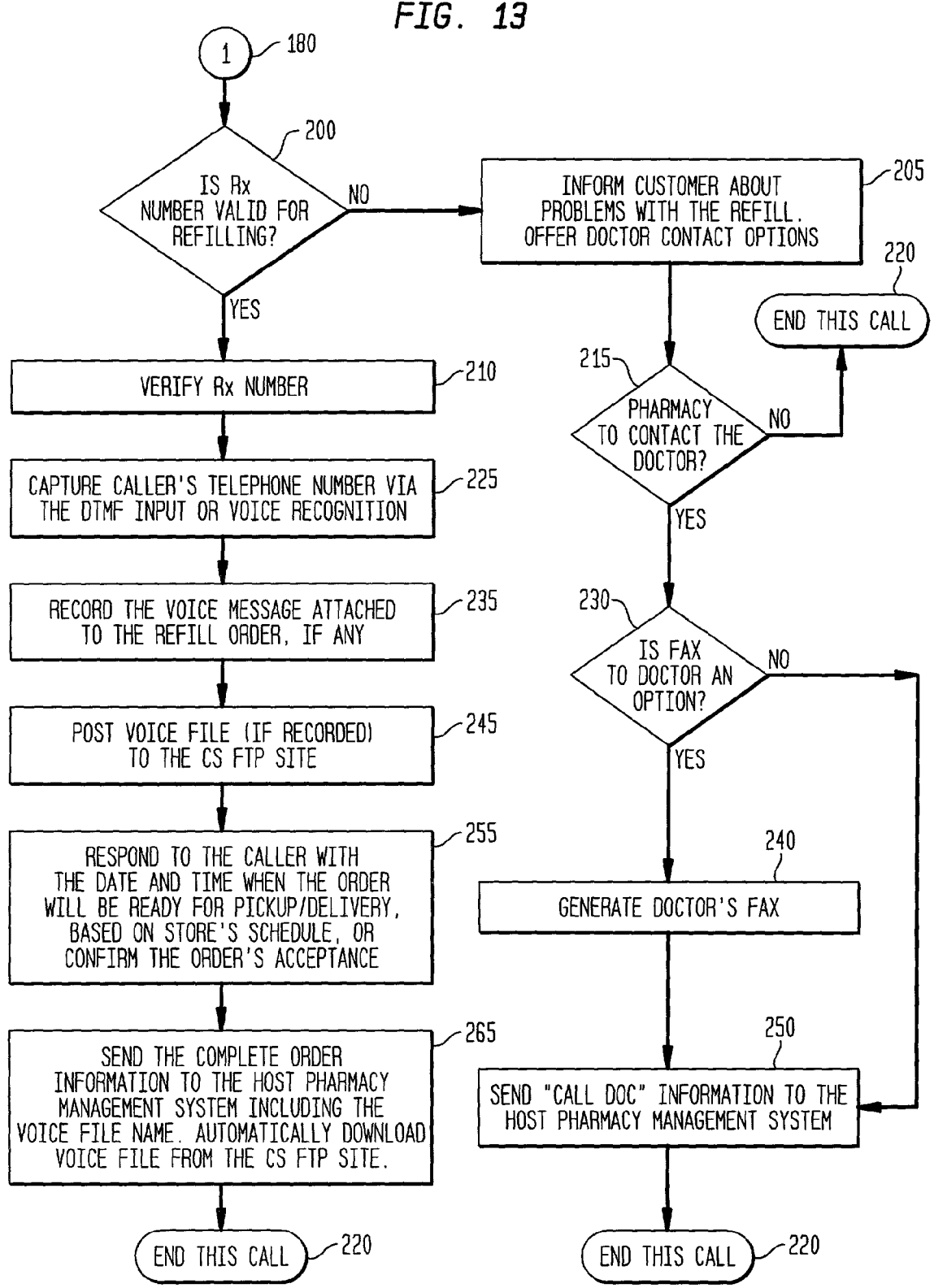
FIG. 13 is a flow chart of another portion of the process of the embodiment of the invention shown in FIG. 11.

Referring back to block 155, after the formatted refill request is sent to the pharmacy management host system over the Internet, another process is invoked at 180. Referring to FIG. 13, if the pharmacy management system checks to determine if the prescription number is valid for refilling at 200. If yes, the prescription number is verified at 210 and the caller's telephone number is captured via DTMF input or voice recognition at 225. A voice message accompanying the refill order is recorded, if any, at 235 and posted to the central server FTP site at 245. At 255 a response is sent to the caller with the date and time when the order will be ready for pickup/delivery based on store schedule, or confirm the order acceptance. At 260 the complete order information is sent to the host pharmacy management system including the voice file name. The voice file is automatically downloaded from the central station FTP site. Then the call is ended at 220. If the prescription number is not valid for refilling at 200, the customer is informed about problems with the refill and is offered doctor contact options at 205. The option for the pharmacy to contact the doctor is provided at 215. If yes, the central station determines whether sending a fax to the doctor is an option at 230. If yes, a fax is generated to the doctor at 240 and at 250 "call doc" information is sent to the pharmacy management system and the call is ended. If the pharmacy is not able to contact the doctor at 215, the call is ended at 220. If faxing to the doctor is not an option than a "call doc" message is sent to the pharmacy management system at 250 and the call is ended at 220.

Figure 14:
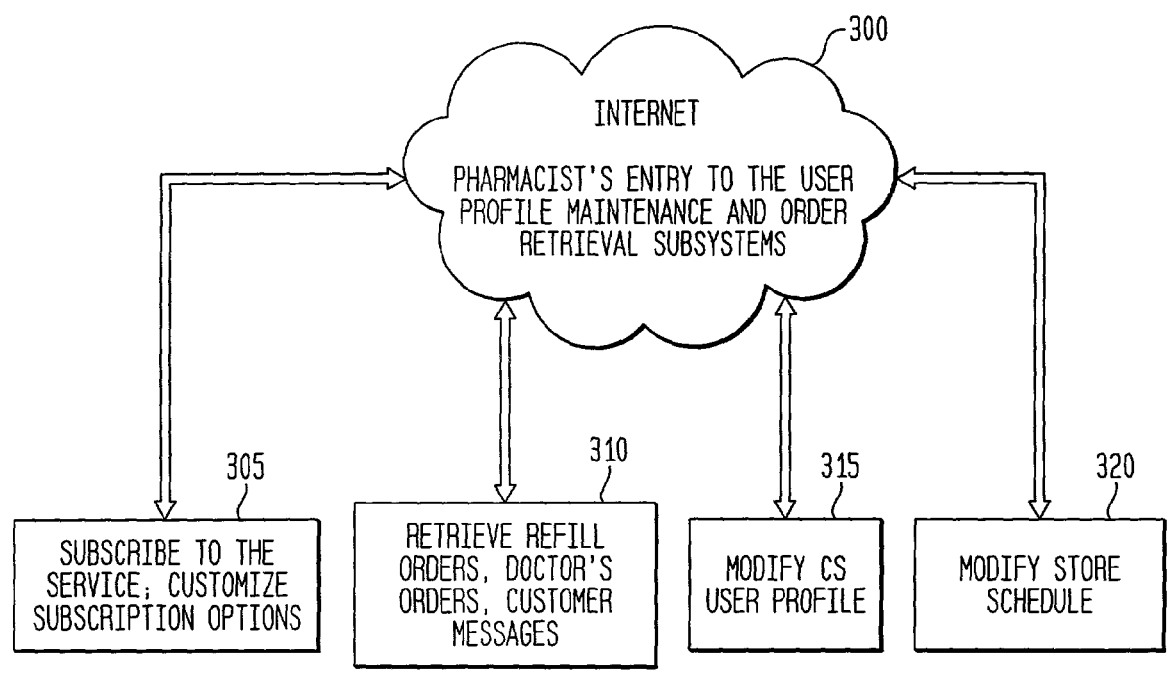
FIG. 14 is a schematic diagram for pharmacist customization and refill retrieval.

FIG. 14 shows where the pharmacist enters the user profile maintenance and order retrieval sub-systems. At 305, the pharmacist can subscribe to the service and customize subscription options. At 310, the pharmacist retrieves refill orders, doctor's orders and customer messages. At 315, the pharmacist can modify the central station user profile. At 320, the pharmacist modifies the stored schedule.

Having thus described the invention in detail, it is to be understood that the foregoing description is not intended to limit the spirit and scope thereof. What is desired to be protected by Letters Patent is set forth in the appended claims.

What is claimed is:

1. A method for refilling prescriptions comprising:
providing a first computer system at a central station remote from a pharmacy;
receiving at the first computer system at the central station a telephone call from a caller relating to a prescription refill request;
obtaining refill information from a caller using the first computer system at the central station;
establishing a first communication path between the first computer system at the central station and a second computer system remote from the central station;
requesting refill authorization from the second computer system by the first computer system at the central station using the first communication path;
if a refill authorization is not obtained by the first computer system, automatically contacting a doctor's office using the first computer system to request a refill authorization from the doctor's office; and
if a refill authorization is obtained by the first computer system,
communicating a refill confirmation to a caller during a call,
establishing a second communication path between the second computer system and a third computer system at a pharmacy,
transmitting the refill information to the third computer system at the pharmacy over the second communication path, and
re-filling the prescription at the pharmacy.

2. The method of claim 1 wherein the refill information is transmitted over the Internet.

3. The method of claim 1 wherein the second computer system comprises a pharmacy management computer system at the pharmacy.

4. The method of claim 1 wherein the first computer system at the central station advises a caller of relevant information received by the first computer system at the central station from the second computer system.

5. The method of claim 1 wherein the first communication path comprises a modem connection.

6. The system of claim 1, wherein the first computer system at the central station records a voice message from the caller and transmits the voice message to the second computer system remote from the central station.

7. A method for refilling prescriptions comprising:
providing a first computer system at a central station remote from a pharmacy;
receiving at the first computer system a telephone call from a caller relating to a prescription refill request;
obtaining refill information from a caller using the first computer system;
requesting using the first computer system a refill authorization from a second computer system remote from the first computer system;
if a refill authorization is not obtained from the second computer system, automatically contacting a doctor's office from a third computer system at a pharmacy to request a refill authorization from the doctor's office; and
if a refill authorization is obtained from the second computer system or from the doctor's office,
communicating a refill confirmation to a caller during a call,
transmitting the refill information to the third computer system at the pharmacy, and
re-filling the prescription at the pharmacy.

8. The method of claim 7 wherein the refill information is transmitted over the Internet.

9. The method of claim 7 wherein the second computer system comprises a pharmacy management computer system at the pharmacy.

10. The method of claim 7 wherein the first computer system advises a caller of relevant information received by the first computer system from the second computer system.

11. The system of claim 7, wherein the first computer system records a voice message from the caller and transmits the voice message to the second computer system.

* * * * *

UNITED STATES PATENT AND TRADEMARK OFFICE
CERTIFICATE OF CORRECTION

| | |
|---|---|
| PATENT NO. | : 7,848,934 B2 |
| APPLICATION NO. | : 09/858877 |
| DATED | : December 7, 2010 |
| INVENTOR(S) | : Paul Kobylevsky et al. |

It is certified that error appears in the above-identified patent and that said Letters Patent is hereby corrected as shown below:

Title Page, item 56 in the References Cited Section, under Other Publications, on Page 3 of the issued patent, in the second column, line 41, the application number "10/641,307" should be deleted and replaced with "10/941,307."

Column 6, line 36, the word "stems" should be deleted, and should be replaced with the word "steps."

Column 8, line 32, the word "length" should be deleted, and should be replaced with the word "lengths."

Column 8, line 61, the word "way" should be deleted, and should be replaced with the word "ways."

Column 9, line 9, the word "Wvhen" should be deleted, and should be replaced with the word "When."

Column 11, line 62, after the word "during," the following should be inserted: --one day can be entered thus creating 'breaks' in the schedule. For example, one may create--

Column 13, line 59, the word " doctor∝s" should be deleted, and should be replaced with the word "doctor's."

Column 14, line 50, the word "want" should be deleted.

Column 15, line 64, the word "comer" should be deleted, and should be replaced with the word "corner."

Column 16, line 61, the word "fuiture" should be deleted, and should be replaced with the word "future."

Column 24, line 2, the word "re" should be deleted, and should be replaced with the word "are."

Signed and Sealed this
Twenty-sixth Day of April, 2011

David J. Kappos
*Director of the United States Patent and Trademark Office*

CERTIFICATE OF CORRECTION (continued)
U.S. Pat. No. 7,848,934 B2

Column 26, line 47, the word " doctor∝s" should be deleted, and should be replaced with the word "doctor's."

Column 29, line 58, the "." should be deleted, and should be replaced with a ","